(12) United States Patent
Thiagarajan et al.

(10) Patent No.: US 12,396,709 B2
(45) Date of Patent: Aug. 26, 2025

(54) ULTRASOUND PROBE AND METHOD OF MAKING THE SAME

(71) Applicant: General Electric Company, Schenectady, NY (US)

(72) Inventors: Naveenan Thiagarajan, Niskayuna, NY (US); Warren Lee, Niskayuna, NY (US); Brian Magann Rush, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 516 days.

(21) Appl. No.: 16/212,863

(22) Filed: Dec. 7, 2018

(65) Prior Publication Data

US 2020/0178941 A1    Jun. 11, 2020

(51) Int. Cl.
*A61B 8/00* (2006.01)
*B33Y 10/00* (2015.01)
*G01N 29/22* (2006.01)
*G01N 29/32* (2006.01)

(52) U.S. Cl.
CPC ............ *A61B 8/546* (2013.01); *A61B 8/4455* (2013.01); *A61B 8/4483* (2013.01); *A61B 8/56* (2013.01); *B33Y 10/00* (2014.12); *G01N 29/226* (2013.01); *G01N 29/326* (2013.01)

(58) Field of Classification Search
CPC ... A61B 8/4444; A61B 8/4455; A61B 8/4483; A61B 8/546; A61B 8/56; B33Y 10/00; G01N 29/226; G01N 29/326
See application file for complete search history.

(56) References Cited

U.S. PATENT DOCUMENTS

| | | | |
|---|---|---|---|
| 5,213,103 A | | 5/1993 | Martin et al. |
| 5,545,942 A | * | 8/1996 | Jaster ................... G10K 11/004 310/341 |
| 5,560,362 A | * | 10/1996 | Sliwa, Jr. ............. G10K 11/004 600/459 |
| 5,721,463 A | | 2/1998 | Snyder |
| 5,961,465 A | * | 10/1999 | Kelly, Jr. ............... A61B 8/546 600/459 |

(Continued)

FOREIGN PATENT DOCUMENTS

| | | |
|---|---|---|
| EP | 1707122 B1 | 4/2010 |
| WO | 2017027654 A1 | 2/2017 |

OTHER PUBLICATIONS

PCT application PCT/US2019/064822 filed Dec. 6, 2019; International Search Report/Written Opinion issued Mar. 27, 2020, 10 pages.

(Continued)

*Primary Examiner* — Ashley K Buran
*Assistant Examiner* — Maria Christina Talty
(74) *Attorney, Agent, or Firm* — McCoy Russell LLP

(57) ABSTRACT

An ultrasound probe is presented. The ultrasound probe includes an ultrasound probe handle. Moreover, the ultrasound probe also includes a phase change chamber monolithic with respect to a portion of the ultrasound probe handle, where the phase change chamber includes hermetic chamber walls extending around and defining an enclosed chamber and a material disposed within the hermetic chamber walls, where the material is configured to change phase in response to heat from a component of the ultrasound probe.

18 Claims, 11 Drawing Sheets

(56) References Cited

U.S. PATENT DOCUMENTS

| | | |
|---|---|---|
| 7,105,986 B2 | 9/2006 | Wildes et al. |
| 7,314,447 B2 | 1/2008 | Park et al. |
| 2006/0191344 A1* | 8/2006 | Hashimoto ............ A61B 8/546 |
| | | 73/632 |
| 2011/0018395 A1* | 1/2011 | Ruffa .................... B06B 1/0618 |
| | | 310/334 |
| 2011/0301508 A1* | 12/2011 | Sethuraman ........... A61N 7/022 |
| | | 601/2 |
| 2012/0060610 A1* | 3/2012 | Oaks .................... A61B 8/4444 |
| | | 73/632 |
| 2013/0303918 A1* | 11/2013 | Miyajima ............ A61B 8/4444 |
| | | 600/459 |
| 2015/0289413 A1 | 10/2015 | Rush et al. |
| 2016/0077059 A1* | 3/2016 | Chung ............... G01N 29/2406 |
| | | 73/620 |
| 2017/0020490 A1* | 1/2017 | Ryu ..................... A61B 8/4427 |
| 2017/0043189 A1* | 2/2017 | Stoddard ................ G10K 11/24 |
| 2017/0065259 A1* | 3/2017 | Pinch ..................... A61B 8/546 |
| 2017/0164926 A1 | 6/2017 | Spicci et al. |
| 2018/0125461 A1 | 5/2018 | Clark et al. |

OTHER PUBLICATIONS

Saunders et al., "Ultrasound transducer self heating: development of 3-D finite-element models", Journal of Physics Conference Series, pp. 72-77, Aug. 2004.

Chabok et al., "Ultrasound Transducer Array Fabrication Based on Additive Manufacturing of Piezocomposites", ASME/ISCIE 2012 International Symposium on Flexible Automation, pp. 433-444, Jun. 2012.

Patankar et al., "A time-stepping analytical model for 3D transient vapor chamber transport", 2017 16th IEEE Intersociety Conference on Thermal and Thermomechanical Phenomena in Electronic Systems (ITherm), pp. 1075-1087, Orlando, Jun. 2017.

* cited by examiner

ULTRASOUND PROBE AND METHOD OF MAKING THE SAME

BACKGROUND

Embodiments of the present specification generally relate to ultrasound imaging and more specifically to an ultrasound probe having a thermal management assembly and a method of making the same.

Ultrasound imaging provides a relatively inexpensive method of imaging. During the process of ultrasound scanning, a clinician attempts to capture a view of a certain anatomy which confirms or negates a particular medical condition. Once the clinician is satisfied with the quality of a view or a scan plane, the image is frozen to proceed to a measurement phase.

Recent developments in ultrasound imaging have led to current state of the art ultrasound devices that boast of relatively high image resolutions and ease of use. These developments have in turn led to increased use of ultrasound for clinical research as well as day to day point of care practice. Consequently, the use of ultrasound imaging has been steadily increasing over the years. Moreover, the improved ultrasound technology has led to higher frequency ultrasound probes that are well-suited for imaging relatively shallow anatomical structures, as is generally the case for musculoskeletal imaging.

Notwithstanding the various advantages of ultrasound, an important factor that restricts the use of ultrasound has been the fact that performing ultrasound scanning requires extended operation of an ultrasound probe at high power to render higher image resolution, while maintaining the surface and key component temperatures under their respective limits. Many of the currently available advanced probes are limited thermally owing to the limited surface area available for convection and numerous interfaces in the conductive heat transfer path from the heat dissipating internal components of the probe to the surface of the probe.

Some conventional approaches to ultrasound probe design to improve conductive heat transfer internal to the probe entail use of heat pipes along a heat spreader bonded to a plastic housing. This design of the probe disadvantageously leads to multiple parts and interfaces. Certain other currently available probes include conventional heat pipes that are incorporated with the probes. However, these probes can offer only incremental gains in thermal performance at a cost of significantly increased complexity and part count.

BRIEF DESCRIPTION

In accordance with aspects of the present specification, an ultrasound probe is presented. The ultrasound probe includes an ultrasound probe handle. Moreover, the ultrasound probe also includes a phase change chamber monolithic with respect to a portion of the ultrasound probe handle, where the phase change chamber includes hermetic chamber walls extending around and defining an enclosed chamber and a material disposed within the hermetic chamber walls, where the material is configured to change phase in response to heat from a component of the ultrasound probe.

In accordance with another aspect of the present specification, an imaging system is presented. The imaging system includes an acquisition subsystem configured to acquire image data corresponding to a subject, where the acquisition subsystem includes an ultrasound probe including an ultrasound probe handle and a phase change chamber monolithic with respect to a portion of the ultrasound probe handle, where the phase change chamber includes hermetic chamber walls extending around and defining an enclosed chamber and a material disposed within the hermetic chamber walls, where the material is configured to change phase in response to heat from a component of the ultrasound probe. In addition, the imaging system includes a processing subsystem in operative association with the acquisition subsystem and configured to process the image data to generate one or more images corresponding to the subject.

In accordance with yet another aspect of the present specification, a method is presented. The method includes additively fabricating first and second segments of an ultrasound probe handle, where at least one of the first and second segments includes a phase change chamber monolithic with respect to the respective segment and including hermetic chamber walls extending around and defining an enclosed chamber, and a material disposed within the hermetic chamber walls, and where the material is configured to change phase in response to heat from one or more components of the ultrasound probe. Furthermore, the method includes operatively coupling the first and second segments.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Ultrasound imaging is being increasingly used to image anatomical regions of interest in a patient. As will be appreciated, an important factor that restricts the use of ultrasound at high power to render higher image resolution is the requirement to maintain the surface and key component temperatures under their respective limits. Systems and methods of the present application present an exemplary design of a three-dimensional (3D) phase change chamber that is configured to provide a thermal management structure for an ultrasound probe. The phase change chamber may be in the form of a 3D vapor chamber (VC), a thermal energy storage chamber, or a combination thereof. Also, the phase change chamber provides enhanced heat transport from internal heat generating components of the ultrasound probe to an outer surface of the phase change chamber for cooling by the ambient environment and/or to phase change material volumes for thermal energy absorption and storage. Additionally, the phase change chamber may also be configured to provide a mechanical support structure for the ultrasound probe.

It may be noted that although the various systems and methods are described in the context of a medical imaging system, these systems and methods may also be used in the imaging of non-living objects such as but not limited to pipes, tubes, luggage, packages, and the like.

Figure 1:
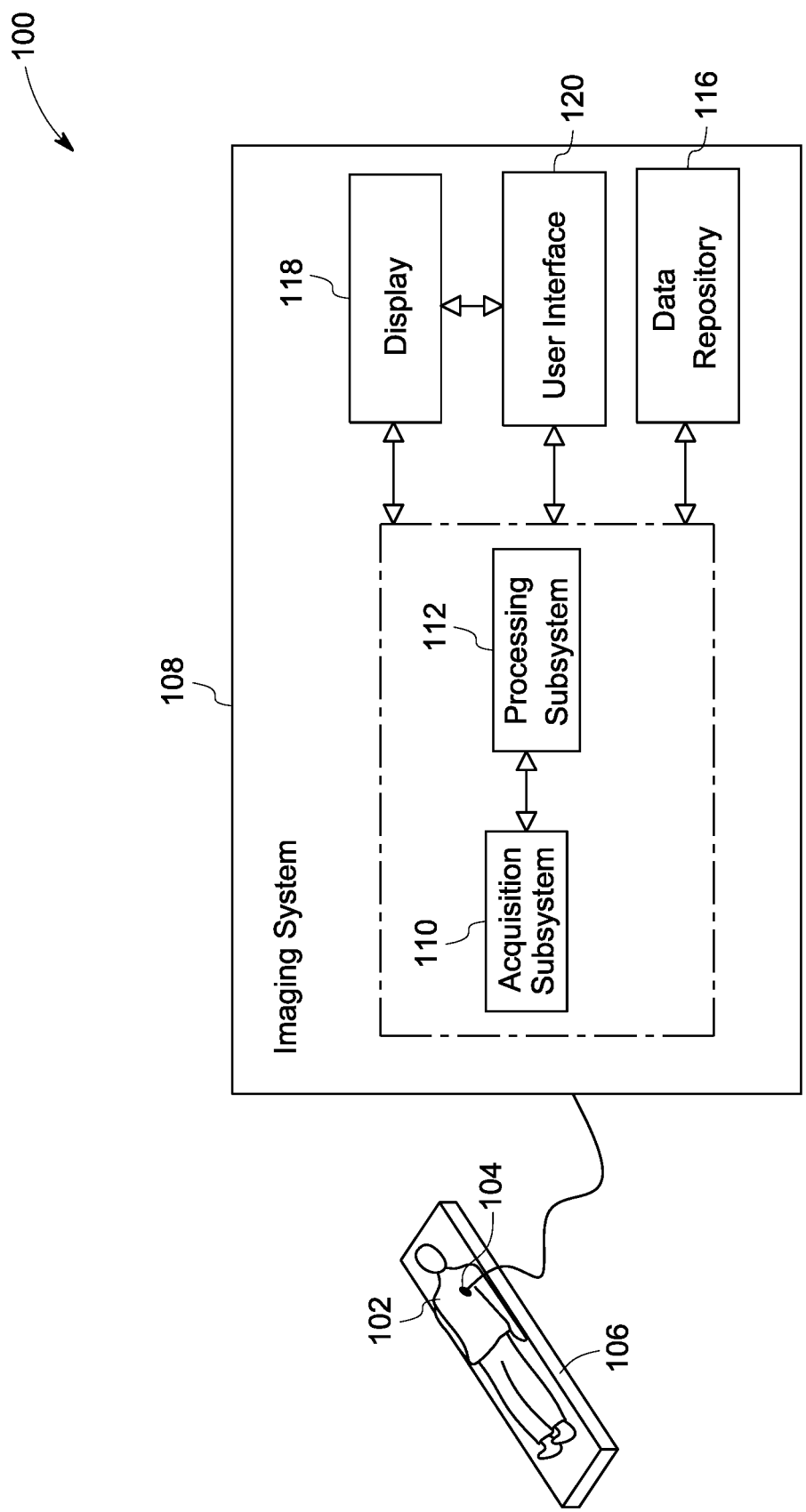
FIG. 1 is a diagrammatical illustration of a system for ultrasound imaging, in accordance with aspects of the present specification.

FIG. 1 is a block diagram of an exemplary system 100 for use in diagnostic imaging, in accordance with aspects of the present specification. More particularly, the system 100 is configured to aid a clinician in imaging a patient 102 to deliver consistent clinical outcomes.

During imaging, the clinician typically positions an image acquisition device on or about a region of interest in a patient 102 being imaged. In one example, the patient 102 may be positioned in a supine position on a patient support 106. Furthermore, an image acquisition device 104 that is operatively coupled to a medical imaging system 108 may be used to acquire image data corresponding to an object or a region of interest in the patient 102. In one embodiment, the image acquisition device 104 may be a probe configured to acquire image data corresponding to one or more anatomical regions of interest in the patient 102.

In a presently contemplated configuration, the system 100 may be configured to acquire image data representative of the patient 102 via the image acquisition device 104. Also, in one embodiment, the probe 104 may include an invasive probe or a non-invasive or external probe, such as an external ultrasound probe, that is configured to aid in the acquisition of image data. In one example, the image acquisition device 104 may include a two-dimensional (2D) or a three-dimensional (3D) ultrasound probe. Additionally, the probe 104 may be a wired probe or a wireless probe. Also, in certain other embodiments, image data may be acquired via one or more sensors (not shown) that may be disposed on the patient 102. By way of example, the sensors may include physiological sensors (not shown) such as positional sensors. In some embodiments, the positional sensors may include electromagnetic field sensors or inertial sensors. These sensors may be operatively coupled to a data acquisition device, such as an imaging system, via leads (not shown), for example.

It may also be noted that although the embodiments illustrated herein are described in the context of an ultrasound probe, other types of probes such as endoscopes, laparoscopes, surgical probes, probes adapted for interventional procedures, or combinations thereof are also contemplated in conjunction with the present specification. An external probe may also be employed in situations where a user such as a sonographer guiding an imaging procedure is located at a remote location and therefore unable to see the probe or the patient 102.

Furthermore, in one example, the acquired image data may include a two-dimensional (2D)) B-mode ultrasound image. Also, in certain embodiments, the image data may include pre-scan-converted or radio frequency (RF) ultrasound data. Additionally, the 2D images may include static 2D images or cine loops that include a series of 2D images or image frames acquired over time. It may be noted that the acquired image data may include 2D ultrasound images, 3D ultrasound images, four-dimensional (4D) ultrasound images, or combinations thereof. Other modes of ultrasound imaging such as Doppler modes of ultrasound imaging may also be used to acquired image data. Some non-limiting examples of the Doppler modes of ultrasound imaging include color, pulsed wave, continuous wave, power doppler, and the like.

Additionally, in one example, the medical imaging system 108 is an ultrasound imaging system. The ultrasound imaging system 108 is in operative association with the image acquisition device 104 and is configured to receive ultrasound image data corresponding to the patient 102 and process the ultrasound image data to generate one or more images corresponding to the patient 102.

It should be noted that although the exemplary embodiments illustrated hereinafter are described in the context of a medical imaging system, other imaging systems and applications such as industrial imaging systems and non-destructive evaluation and inspection systems, such as pipeline inspection systems, liquid reactor inspection systems, are also contemplated. Additionally, the exemplary embodiments illustrated and described hereinafter may find application in multi-modality imaging systems that employ ultrasound imaging in conjunction with other imaging modalities, position-tracking systems or other sensor systems. In one example, the multi-modality imaging system may include a positron emission tomography (PET) imaging system-ultrasound imaging system. Furthermore, in other non-limiting examples of the multi-modality imaging systems, the ultrasound imaging system may be used in conjunction with other imaging systems, such as, but not limited to, a computed tomography (CT) imaging system, a contrast enhanced ultrasound imaging system, an X-ray imaging system, an optical imaging system, a magnetic resonance (MR) imaging system, an optical imaging system, virtual/augmented reality imaging systems, and other imaging systems, in accordance with aspects of the present specification.

As noted hereinabove, in a presently contemplated configuration, the medical imaging system 108 is an ultrasound imaging system. Further, the medical imaging system 108 may include an acquisition subsystem 110 and a processing subsystem 112, in one embodiment. Moreover, the acquisition subsystem 110 of the medical imaging system 108 is configured to receive image data representative of the patient 102 from the image acquisition device 104, in one embodiment. For example, the acquired image data may include a plurality of 2D ultrasound images or slices. In other embodiments, 3D images or 4D images may be acquired. It may be noted that the terms images and image frames may be used interchangeably.

In addition, the acquisition subsystem 110 may also be configured to acquire images stored in the optical data storage article. It may be noted that the optical data storage article may be an optical storage medium, such as a compact disc (CD), a digital versatile disc (DVD), multi-layer structures, such as DVD-5 or DVD-9, multi-sided structures, such as DVD-10 or DVD-18, a high definition digital versatile disc (HD-DVD), a Blu-ray disc, a near field optical storage disc, a holographic storage medium, or another like volumetric optical storage medium, such as, for example, two-photon or multi-photon absorption storage format. Further, the 2D images so acquired by the acquisition subsystem 110 may be stored locally on the medical imaging system 108 in a data repository 116, for example.

Moreover, the image data acquired from the patient 102 may then be processed by the processing subsystem 112. The processing subsystem 112, for example, may include one or more application-specific processors, graphical processing units, digital signal processors, microcomputers, microcontrollers, Application Specific Integrated Circuits (ASICs), Field Programmable Gate Arrays (FPGAs), Programmable Logic Arrays (PLAs), and/or other suitable processing devices. Alternatively, the processing subsystem 112 may be configured to store the acquired image data and/or the user input in the data repository 116 for later use. In one embodiment, the data repository 116, for example, may include a hard disk drive, a floppy disk drive, a compact disk-read/write (CD-R/W) drive, a Digital Versatile Disc (DVD) drive, a flash drive, and/or a solid-state storage device.

The image data acquired and/or processed by the medical imaging system 108 may be employed to generate an ultrasound image that is used to aid a clinician in making measurements and/or providing a diagnosis based on the generated image. In certain embodiments, the processing subsystem 112 may be further coupled to a storage system, such as the data repository 116, where the data repository 116 is configured to store the generated image(s). In certain embodiments, the data repository 116 may include a local database.

Moreover, as illustrated in FIG. 1, the medical imaging system 108 may include a display 118 and a user interface 120. In certain embodiments, such as in a touch screen, the display 118 and the user interface 120 may overlap. Also, in some embodiments, the display 118 and the user interface 120 may include a common area. In accordance with aspects of the present specification, the display 118 of the medical imaging system 108 may be configured to display an image generated by the medical imaging system 108 based on the acquired image data.

In addition, the user interface 120 of the medical imaging system 108 may include a human interface device (not shown) configured to aid the clinician in manipulating image data displayed on the display 118. The human interface device may include a mouse-type device, a trackball, a joystick, a stylus, or a touch screen configured to facilitate the clinician to identify the one or more regions of interest in the images. However, as will be appreciated, other human interface devices, such as, but not limited to, a touch screen, may also be employed. Furthermore, in accordance with aspects of the present specification, the user interface 120 may be configured to aid the clinician in navigating through the images acquired by the medical imaging system 108. Additionally, the user interface 120 may also be configured to aid in manipulating and/or organizing the displayed images and/or generated indicators displayed on the display 118.

Figure 2:
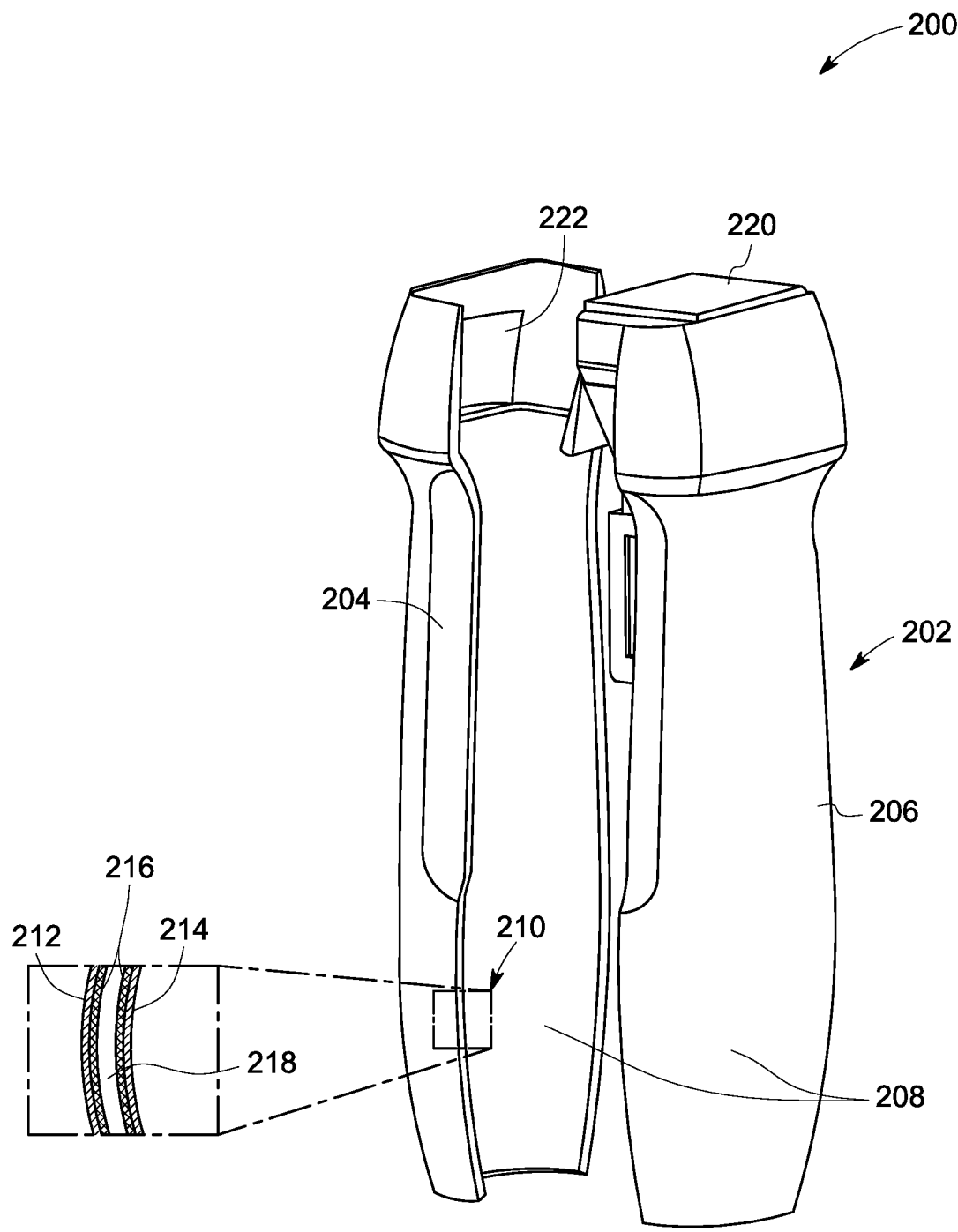
FIGS. 2-5 are diagrammatical illustrations of different embodiments of an ultrasound probe having various configurations of a thermal management assembly in the form of a phase change chamber, where the ultrasound probe is configured for use in the system of FIG. 1, in accordance with aspects of the present specification.

As noted hereinabove, an important factor that restricts the use of ultrasound has been the fact that performing ultrasound scanning requires extended operation of an ultrasound probe at high power to render higher image resolution, while maintaining the surface and key component temperatures under their respective limits. FIG. 2 presents an exemplary design of a structure configured for use in an ultrasound probe such as the ultrasound probe 104 of FIG. 1 that circumvents the shortcomings of the presently available ultrasound probes. More particularly, an exemplary design of a 3D thermal management assembly or structure in the form of a phase change chamber that is configured to provide enhanced thermal management for an ultrasound probe is presented. The exemplary phase change chamber may also be configured to simultaneously provide mechanical support to the various components of the ultrasound probe 104.

Referring now to FIG. 2, a diagrammatical illustration 200 of one embodiment of an ultrasound probe for use in the system 100 of FIG. 1 is depicted. FIG. 2 is described in conjunction with the components of FIG. 1.

The ultrasound probe 200 includes an ultrasound probe handle 202. In one embodiment, the ultrasound probe handle 202 may include two or more segments that are operatively coupled to one another. In the example depicted in FIG. 2, the ultrasound probe handle 202 is depicted as having a first segment 204 and a second segment 206. Also, in FIG. 2, each segment 204, 206 is representative of one half of the ultrasound probe handle 202. It may be noted that in accordance with further aspects of the present specification, use of a single segment or other number of segments for the ultrasound probe handle 202 is also envisaged.

Further, the ultrasound probe 200 includes a thermal management assembly in the form of a phase change chamber 208 that is configured to provide enhanced thermal management for the ultrasound probe 200. The reference number 208 shown in FIG. 2 refers to the interior of the chamber. In particular, the phase change chamber 208 is monolithic with respect to a portion of the ultrasound probe handle 202. The phase change chamber 208 is a monolithic structure configured to thermally interface with one or more heat generating components in the ultrasound probe 200 to dissipate the heat generated by the components of the ultrasound probe 200. In one embodiment, the phase change chamber 208 is thermally coupled to one or more components of the ultrasound probe 200 to facilitate dissipation of heat from the heat generating components of the ultrasound probe 200. Moreover, in certain embodiments, the phase change chamber 208 may include two or more phase change chambers. Further, in certain embodiments, the phase change chamber 208 extends along at least a portion of a wall of the ultrasound probe handle 202. In other embodiments, the phase change chamber 208 forms at least a portion of a wall of the ultrasound probe handle 202.

In one embodiment, the phase change chamber is a three-dimensional (3D) vapor chamber 208. Additionally, the 3D vapor chamber 208 extends along at least two orthogonal directions. Furthermore, the embodiment illustrated in FIG. 2 depicts the phase change chamber 208 as including two 3D vapor chambers. Each 3D vapor chamber 208 corresponds to a segment 204, 206 of the ultrasound probe handle 202. As will be appreciated, the 3D vapor chamber 208 is a heat transfer device that is vacuum sealed. Further, the 3D vapor chamber 208 typically includes an evaporator end and a condenser end. In addition, as depicted in the embodiment of FIG. 2, each of the 3D vapor chambers 208 is designed in the shape of a corresponding segment 204, 206 of the ultrasound probe handle 202.

Moreover, the 3D vapor chamber 208 has hermetic chamber walls that extend around and define an enclosed chamber. Additionally, a material is disposed within the hermetic chamber walls. This material is configured to change phase in response to heat received from a component of the ultrasound probe 200. In the example of FIG. 2, the material is a working fluid that is configured to transition between a liquid phase and a vapor phase. It may be noted that in certain embodiments, the hermetic chamber walls may include openings or ports. In one example, these openings or ports may be used to fill the working fluid within the chamber walls.

Reference numeral 210 is used to represent an expanded view of a cross-section of one embodiment of the enclosed chamber of the 3D vapor chamber 208. In certain embodiments, the 3D vapor chamber 208 includes an external wall 212 and an internal wall 214. Moreover, each of the external wall 212 and the internal wall 214 includes an interior surface and an exterior surface. Also, a cavity is formed between the external wall 212 and the internal wall 214.

Additionally, the 3D vapor chamber 208 includes a porous wick structure 216 configured to facilitate transport of the working fluid in the 3D vapor chamber 208. In particular, the porous wick structure 216 is disposed such that the porous wick structure 216 lines one or more interior surfaces of the external wall 212 and/or the internal wall 214 of the 3D vapor chamber 208. In some embodiments, the porous wick structure 216 may be formed on interior surfaces of the external and internal walls 212, 214. The porous wick structure 216 includes pores that are configured to hold the working fluid in the liquid phase. More particularly, the pores in the porous wick structure 216 are configured to hold the working fluid in the liquid phase in the 3D vapor chamber 204 until heat received from a heat generating component of the ultrasound probe 200 vaporizes the working fluid into a vapor phase in the enclosed 3D vapor chamber 208. Also, the porous wick structure 216 aids in returning the working fluid from the condenser end to the evaporator end of the 3D vapor chamber 208.

Also, the 3D vapor chamber 208 includes a vapor transport column or vapor space 218. The vapor transport column 218 is configured to aid in the transport of the working fluid in a vapor phase within the 3D vapor chamber 208.

Moreover, in some embodiments, the 3D vapor chamber 208 may include one or more support columns (not shown in FIG. 2) that extend between the external and internal walls 212, 214. These columns are employed to prevent the external and internal walls 212, 214 from moving toward each other or to reduce the distance by which the external and internal walls 212, 214 move toward each other.

Furthermore, the working fluid such as water is used in the 3D vapor chamber 208 to aid in the transfer of heat from the heat generating components of the ultrasound probe 200. It may be noted that the working fluid is in a liquid phase and housed in the pores of the porous wick structure 216. Once the 3D vapor chamber 208 is placed in contact with a heat source such as a heat generating component in the ultrasound probe 200, the heat from the heat source is absorbed by the working fluid at the evaporator end of the 3D vapor chamber 208. The absorbed heat results in the working fluid being transformed from a liquid phase to a vapor phase. The working fluid in the vapor phase travels from the evaporator end toward the condenser end via the vapor transport column 218 of the 3D vapor chamber 208. Subsequently, the working fluid in the vapor phase is cooled at the condenser end by releasing the latent heat. In some embodiments, the latent heat is transferred to an outer surface of the 3D vapor chamber 208 and the heat is then dissipated into the surrounding environment. The condensed working fluid is then returned to the evaporator end of the 3D vapor chamber 208 via the porous wick structure 216.

As previously noted, one or more components of the ultrasound probe 200 generate heat during operation of the ultrasound probe 200. Some examples of the heat generating components in the ultrasound probe 200 include a transducer assembly, ASICs, processors, batteries, sensors (not shown in FIG. 2), and the like. Reference numeral 220 is used to depict the transducer assembly in the ultrasound probe 200. It is desirable to efficiently dissipate the heat generated by the internal components of the ultrasound probe 200 such as the transducer assembly 220 to ensure safe and continuous operation of the ultrasound probe 200 to image the patient 102.

In accordance with aspects of the present specification, the 3D vapor chanter 208 is configured to provide enhanced thermal management of the ultrasound probe 200. In particular, the 3D vapor chamber 208 is configured to facilitate enhanced heat transfer from the heat generating components of the ultrasound probe 200 by thermally contacting one or more surfaces of the heat generating components of the ultrasound probe 200. Accordingly, the 3D vapor chamber 208 is in thermal communication with the heat generating components of the ultrasound probe 200. In the example of FIG. 2, the transducer assembly 220 is thermally coupled to the 3D vapor chamber 208 of the ultrasound probe 200. More specifically, in one example, the internal wall 214 is configured to be in thermal communication with the heat generating components such as the transducer assembly 220 of the ultrasound probe 200. Reference numeral 222 is representative of a portion of the internal wall 214 of the 3D vapor chamber 208 that is in direct thermal communication with the transducer assembly 220. In some embodiments, the 3D vapor chamber 208 may be directly thermally coupled to the heat generating components via use of a thermal interface material. Some non-limiting examples of the thermal interface material include thermal pads, grease, adhesive, and the like. By way of a non-limiting example, an adhesive material may be employed to effect a thin adhesive joint between the 3D vapor chamber 208 and the heat generating components of the ultrasound probe 200. Some non-limiting examples of the adhesive material include thermally non-conductive epoxy, thermally conductive epoxy, filled epoxy, and the like.

Moreover, the 3D vapor chamber 208 is configured to provide enhanced thermal management in the ultrasound probe 200 by absorbing the heat/thermal energy generated by the heat generating components of the ultrasound probe 200. The heat absorbed by the 3D vapor chamber 208 is in turn transferred to the working fluid in the 3D vapor chamber 208. As the working fluid absorbs the heat, the working fluid in the liquid phase is transformed to a gas/vapor phase. The working fluid in the vapor/gas phase then travels down in the vapor transport column 218 toward the condenser end of the 3D vapor chamber 208 where the working fluid in the vapor phase is cooled, releasing its latent heat. In particular, the heat is transferred from the working fluid to an outer surface of the 3D vapor chamber 208 and is dissipated to the surrounding environment. Subsequent to the cooling, the working fluid is transformed from the vapor phase to the liquid phase. The porous wick structure 216 and capillary action aid in recirculating the working fluid in the liquid phase to the evaporator end, where the working fluid once again absorbs thermal energy from the external and/or internal walls 212, 214 of the 3D vapor chamber 208.

Further, to facilitate rapid and efficient removal/dissipation of heat or thermal energy from internal components of the ultrasound probe 200, the 3D vapor chamber 208 is formed using a material with a high thermal conductivity. By way of example, the 3D vapor chamber 208 may be formed using materials such as, but not limited to, titanium, aluminum, copper, and the like.

It may be noted that for ease of illustration and description, the 3D vapor chamber 208 is depicted as including two 3D vapor chamber portions. These portions may be sealed to form the 3D vapor chamber 208. Accordingly, in one embodiment, the 3D vapor chamber 208 is a continuous structure.

The ultrasound probe 200 including the ultrasound probe handle 202 and the 3D vapor chamber 208 may be formed using additive manufacturing, such as by being formed using three-dimensional (3D) printing, rapid prototyping (RP), direct digital manufacturing (DDM), selective laser melting (SLM), electron beam melting (EBM), direct metal laser melting (DMLM), and the like. Some other exemplary methods of additive fabricating usable with the present specification may include processes, such as, but not limited to, direct writing, electron beam deposition, laser deposition, stereo-lithography, and the like. Alternatively, the ultrasound probe 200 may be formed in any another manner.

Additionally, the porous wick structure 216 may also be formed using additive manufacturing and may be formed from sintered powder. Alternatively, the porous wick structure 216 may be formed using other techniques and/or from other materials. It may be noted that in certain embodiments, the porous wick structure 216 may line the entire interior surface of the hermetic external and internal chamber walls 212, 214 of the 3D vapor chamber 208 and is configured to hold the working fluid in the liquid phase.

Additively manufacturing the 3D vapor chamber 204 as described hereinabove results in a 3D vapor chamber 208 that is a single, monolithic structure and configured to interface with one or more heat sources in the ultrasound probe 200 to facilitate the enhanced dissipation of heat generated by the internal components of the ultrasound probe 200. In particular, the 3D vapor chamber 208 is configured to facilitate transfer of thermal energy from the heat generating components of the ultrasound probe 200 such as the transducer assembly 220 and internal electronics of the ultrasound probe 200 to the outer surface of the 3D vapor chamber 208 for cooling by the ambient environment.

In accordance with aspects of the present specification, in some embodiments, at least a portion of the 3D vapor chamber 208 is configured to conform to a shape of the ultrasound probe handle 202 of the ultrasound probe 200. Accordingly, in this example, the 3D vapor chamber 208 conforms to the shape of the ultrasound probe handle 202. In other embodiments, an outer coating such as an outer electrically insulating cover may be disposed on an outer/exterior surface of the 3D vapor chamber 208. In this example, the 3D vapor chamber 208 having the outer coating forms the ultrasound probe handle 202 of the ultrasound probe 200.

In yet another embodiment, the 3D vapor chamber 208 is configured to conform to the shape of one or more components of the ultrasound probe 200. In this example, the 3D vapor chamber 208 may conform to one or more aspects of the shape of the component. By way of example, if the component has a shape of a cube, then the 3D vapor chamber 208 may be configured to conform to one or more faces of the cube. Moreover, in this example, the 3D vapor chamber 208 is an internal structure that conforms to the shape of the internal components of the ultrasound probe 200. Furthermore, in one embodiment, an outer shell that encompasses the 3D vapor chamber 208 may be disposed around the 3D vapor chamber 208. Accordingly, in this example, the outer shell functions as the ultrasound probe handle 200 of the ultrasound probe 200. Moreover, the 3D vapor chamber 208 forms an ergonomic exterior shape of the ultrasound probe handle 202 of the ultrasound probe 200.

Accordingly, the design of the ultrasound probe 200 having the 3D vapor chamber 208 provides enhanced thermal management in the ultrasound probe 200 via the 3D vapor chamber 208. As will be appreciated, the currently available techniques rely on the thermal conductivity of material such as copper and titanium to transport the heat. However, the exemplary 3D vapor chamber 208 uses evaporation and condensation of the working fluid to transport the heat in the 3D vapor chamber 208. Consequently, use of the 3D vapor chamber 208 provides up to a 20× improvement over that provided via use of copper for heat transportation.

In accordance with further aspects of the present specification, in addition to facilitating enhanced thermal management in the ultrasound probe 200, the 3D vapor chamber 208 may also be configured to provide mechanical support to the internal components of the ultrasound probe 200. This aspect will be described in greater detail with reference to FIGS. 6-9.

Figure 3:
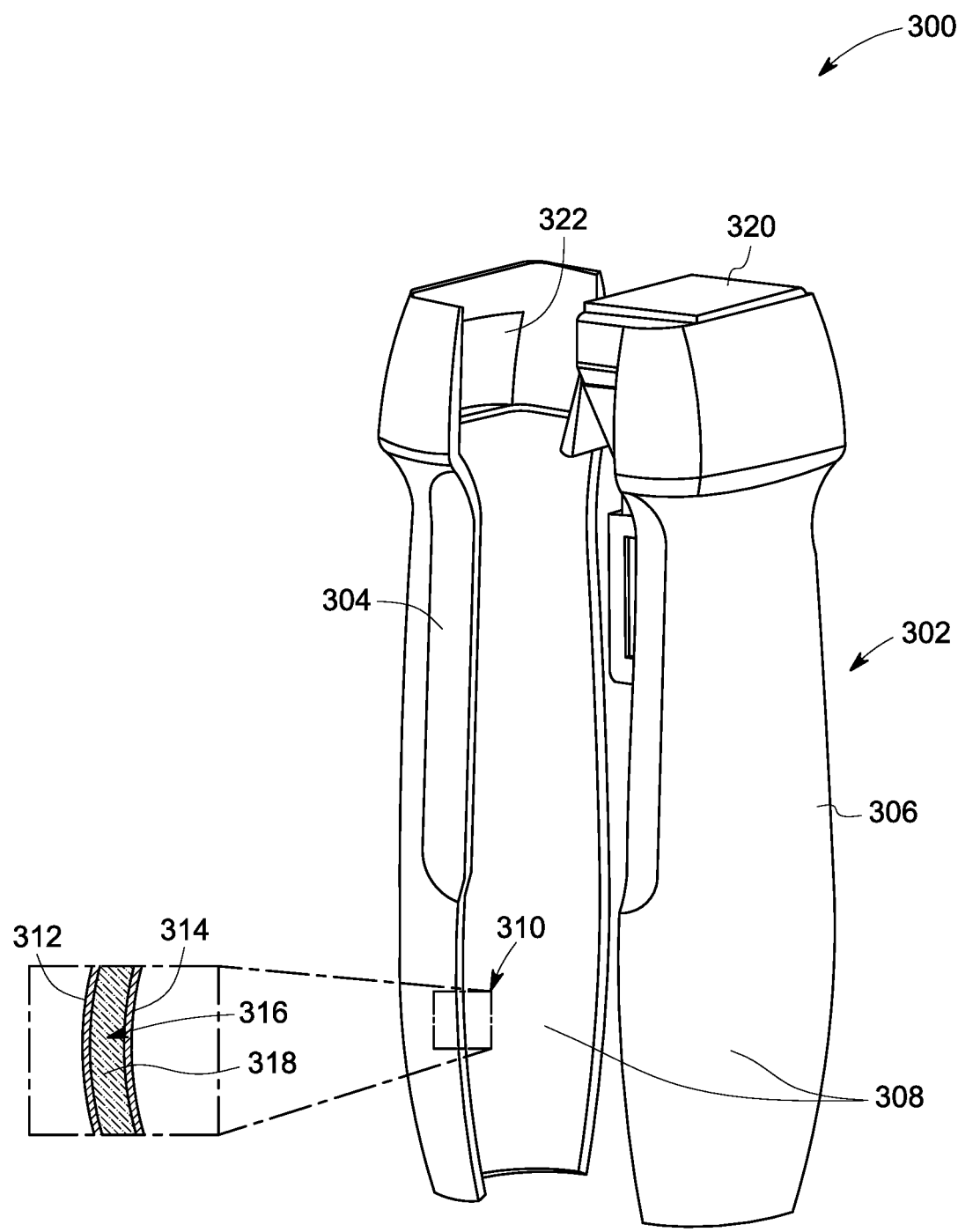

Turning now to FIG. 3, a diagrammatical illustration 300 of another embodiment of an ultrasound probe for use in the system 100 of FIG. 1 is depicted. FIG. 3 is described in conjunction with the components of FIGS. 1-2.

The ultrasound probe 300 includes an ultrasound probe handle 302. As previously described with reference to FIG. 2, in certain embodiments, the ultrasound probe handle 302 may include two or more segments that are operatively coupled to one another. FIG. 3 depicts the ultrasound probe handle 302 as having a first segment 304 and a second segment 306. Each segment 304, 306 is representative of one half of the ultrasound probe handle 302. In accordance with further aspects of the present specification, use of a single segment or other number of segments for the ultrasound probe handle 302 is envisioned.

In addition, the ultrasound probe 300 includes a thermal management assembly in the form of a phase change chamber 308 that is configured to provide enhanced thermal management for the ultrasound probe 300. The reference number 308 shown in FIG. 3 refers to the interior of the chamber. As previously noted, that the phase change chamber 308 is monolithic with respect to a portion of the ultrasound probe handle 302 and is configured to thermally interface with one or more heat generating components in the ultrasound probe 300 to dissipate the heat generated by the components of the ultrasound probe 300. Further, in certain embodiments, the phase change chamber 308 may include two or more phase change chambers.

In the example illustrated in FIG. 3, the phase change chamber is a thermal energy storage chamber 308. The embodiment illustrated in FIG. 3 depicts the phase change chamber 308 as including two thermal energy storage chambers. Each thermal energy storage chamber 308 corresponds to each segment 304, 306 of the ultrasound probe handle 302. Additionally, as depicted in the embodiment of FIG. 3, each of the thermal energy storage chambers 308 is designed in the shape of a corresponding segment 304, 306 of the ultrasound probe handle 302.

Furthermore, the thermal energy storage chamber 308 has hermetic chamber walls that extend around and define an enclosed chamber and a material is disposed within the hermetic chamber walls. This material is configured to change phase in response to heat received from a component of the ultrasound probe 300. In the example of FIG. 3, the material is a phase change material that is configured to transition between a solid phase and a liquid phase. Further, the phase change material is configured to transition from a first state to a second state to absorb and/or release heat. In some embodiments, the first and second states may be the same, while in some other embodiments, the first and second states may be different. By way of example, the phase change material may transition from a solid state to a liquid state upon receiving a determined level of heat from the component of the ultrasound probe 300. Other non-limiting examples of the transition of the phase change material include a solid-to-solid phase transition, a liquid-to-solid phase transition, or a liquid-to-liquid phase transition. In yet another embodiment, the phase change material may undergo chemical reactions to absorb and/or release heat. Additionally, one or more phase change materials may have the same or different phase transition temperatures. It may be noted that in certain embodiments, the hermetic chamber walls may include openings or ports. In one example, these openings or ports may be used to fill the phase change material within the chamber walls.

Reference numeral 310 is used to represent an expanded view of a cross-section of one embodiment of the enclosed chamber of the thermal energy storage chamber 308. In one embodiment, the thermal energy storage chamber 308 includes an external wall 312 and an internal wall 314. Each of the external wall 312 and the internal wall 314 includes an interior surface and an exterior surface. Also, the external wall 312 and the internal wall 314 form a cavity or space 316.

In the example of FIG. 3, the material that is disposed within the thermal energy storage chamber 308 is a phase change material 318. More particularly, the phase change material 318 is disposed in a cavity 316 between the external and internal walls 312, 314 of the thermal storage energy chamber 308. The phase change material 318 has a solid phase, a liquid phase, or a combination thereof. Also, the phase change material 318 may include materials such as, but not limited to, organic materials, inorganic materials, metallic alloys, eutectic alloys, or combinations thereof. Also, in certain embodiments, the phase change material 318 may also include thermally conductive fillers such as, but not limited to, particles, spheres, and ribbons of materials such as graphite, copper, aluminum, and the like to improve heat transfer. In yet another embodiment, the phase change material 318 may be an encapsulated phase change material where the phase change material is contained within a polymeric shell. Further, the phase change material 318 may be configured to facilitate the bidirectional transfer of heat between the heat generating components of the ultrasound probe 300 and the phase change material 318 in the thermal energy storage chamber 308.

Moreover, in certain embodiments, the thermal energy storage chamber 308 may include one or more support columns (not shown in FIG. 3) that extend between the external and internal walls 312, 314. These columns are employed to prevent the external and internal walls 312, 314 from moving toward each other or to reduce the distance by which the external and internal walls 312, 314 move toward each other.

As previously noted, one or more components of the ultrasound probe 300 generate heat during operation of the ultrasound probe 300. Some examples of the heat generating components in the ultrasound probe 300 include a transducer assembly, ASICs, processors, batteries, sensors (not shown in FIG. 3), and the like. Reference numeral 320 is used to depict the transducer assembly in the ultrasound probe 300. It is desirable to efficiently dissipate the heat generated by the components of the ultrasound probe 300 to ensure safe and continuous operation of the ultrasound probe 300 to image the patient 102.

In accordance with aspects of the present specification, the thermal energy storage chamber 308 is configured to facilitate enhanced thermal management of the ultrasound probe 300. In particular, the thermal energy storage chamber 308 is configured to provide enhanced heat transfer from the heat generating components of the ultrasound probe 300 by directly thermally contacting one or more surfaces of the heat generating components of the ultrasound probe 300. By way of example, in FIG. 3, the transducer assembly 320 is thermally coupled to the thermal energy storage chamber 308 of the ultrasound probe 300. More specifically, the internal wall 314 is configured to be in thermal communication with the heat generating components such as the transducer assembly 320 of the ultrasound probe 300. Reference numeral 322 is used to represent a portion of the internal wall 314 of the thermal energy storage chamber 308 that is in direct thermal communication with the transducer assembly 320. In some embodiments, the thermal energy storage chamber 308 may be directly thermally coupled to the heat generating components via use of a thermal interface material such as, but not limited to, thermal pads, grease, adhesive, and the like. By way of a non-limiting example, an adhesive material such as, but not limited to, thermally non-conductive epoxy, thermally conductive epoxy, filled epoxy, and the like, may be employed to effect a thin adhesive joint between the thermal energy storage chamber 308 and the heat generating components of the ultrasound probe 300.

Moreover, the thermal energy storage chamber 308 is configured to absorb the heat/thermal energy generated by the heat generating components of the ultrasound probe 300. The heat absorbed by the thermal energy storage chamber 308 is in turn transferred to the phase change material 318 for storage in the thermal energy storage chamber 308. As the phase change material 318 absorbs the heat, the phase change material in the solid phase is transformed to a liquid phase. By way of example, the phase change material 318 may absorb the heat from the heat generating component when the heat generating component exceeds the melting point of phase change material 318, thereby lowering the temperature rise of heat generating component. Accordingly, the absorbed heat is stored in the thermal energy storage chamber 308. In certain embodiments, the heat may be transferred to an outer surface of the thermal energy storage chamber 308 and is dissipated to the surrounding environment. It may be noted that in certain embodiments the thermal energy storage chamber 308 is designed such that the phase change material 318 does not impede the heat transfer from the heat generating component through the chamber walls to the surrounding ambient.

In certain embodiments, it may be desirable to dissipate the stored heat to the ambient. Accordingly, in this example, the thermal energy stored in the phase change material 318 in the thermal energy storage chamber 308 may be dissipated to the surrounding environment. Consequent to this dissipation of the stored heat, the phase change material 318 is cooled, thereby transitioning the phase change material 318 from the liquid phase to the solid phase.

In yet another embodiment, it may be desirable to transfer heat to a component of the ultrasound probe 300. In this example, the thermal energy stored in the phase change material 318 in the thermal energy storage chamber 308 may be conveyed to the component to be heated. Consequent to this transfer of heat, the phase change material 318 is cooled, thereby transitioning the phase change material 318 from the liquid phase to the solid phase. Moreover, in other embodiments, the ultrasound probe may include multiple thermal energy storage chambers. In this example, the heat may be transferred from one thermal energy storage chamber to another thermal energy storage chamber.

It may be noted that to facilitate rapid and efficient removal/dissipation of heat or thermal energy from internal components of the ultrasound probe 300, the thermal energy storage chamber 308 is formed using a material with a high thermal conductivity. By way of example, the thermal energy storage chamber 308 may be formed using materials such as, but not limited to, titanium, aluminum, copper, and the like. In some embodiments, the internal walls such as the internal wall 314 may also be retrofitted with heat conducting elements such as heat pipes, copper, graphite sheets, rods, and the like.

Further, for ease of illustration and description, the thermal energy storage chamber 308 is depicted as including two phase change chamber portions. These portions may be sealed to form the thermal energy storage chamber 308. Accordingly, in one embodiment, the thermal energy storage chamber 308 is a continuous structure.

It may also be noted that in some embodiments, the cavity 316 may also include fins (not shown in FIG. 3) extending from the inner surfaces of the external wall 312 and/or the internal wall 314 to aid in heat transport to the phase change material 318. In this example, the fins may be in the form of studs or may extend in an annular fashion around the radius of the ultrasound probe 300. It may be noted that the annular fins may have openings or ports to facilitate filling and/or transport of the phase change material 318. Moreover, it may also be noted that the fins in the cavity 316 of the thermal energy storage chamber 308 are internal fins.

Additionally, in certain embodiments, multiple such fins may be dispersed along the length of the thermal energy storage chamber 308. The fins or studs serve to increase the surface area of the thermal energy storage chamber 308, which in turn improves heat transfer. In certain embodiments, the fins and/or studs may be formed using the same material as the external wall 312 and the internal wall 314 of the thermal energy storage chamber 308. Moreover, as previously noted, the phase change material 318 may also include thermally conductive fillers such as particles, spheres, and/or ribbons of graphite, copper, aluminum, and the like to improve heat transfer.

The ultrasound probe 300 including the ultrasound probe handle 302 and the thermal energy storage chamber 308 may be formed using additive manufacturing, such as by being formed using three-dimensional (3D) printing, rapid prototyping (RP), direct digital manufacturing (DDM), selective laser melting (SLM), electron beam melting (EBM), direct metal laser melting (DMLM), and the like. Some other exemplary methods of additive fabricating usable with the present specification may include processes, such as, but not limited to, direct writing, electron beam deposition, laser deposition, stereo-lithography, and the like. Alternatively, the ultrasound probe 300 may be formed in any another manner such as, but not limited to, casting, welding, machining, and the like. Additively manufacturing the thermal energy storage chamber 308 as described hereinabove results in a thermal energy storage chamber 308 that is a single, monolithic structure and configured to interface with one or more heat sources in the ultrasound probe 300 to facilitate the enhanced dissipation of heat generated by the internal components of the ultrasound probe 300.

In accordance with further aspects of the present specification, the ultrasound probe 300 may include two or more thermal energy storage chambers 308. These thermal energy storage chambers 308 may be distributed within an inner volume of the ultrasound probe 300. Additionally, each of the two or more thermal energy storage chambers may include a corresponding phase change material disposed within a corresponding thermal energy storage chamber. Moreover, each phase change material may have a different melting point, thereby facilitating maintaining different components of the ultrasound probe 300 at different temperatures. In certain other embodiments, the thermal energy storage chambers 308 may be distributed within the volume of phase change chamber due to space constraints.

As previously described with respect to FIG. 2, at least a portion of the thermal energy storage chamber 308 may be configured to conform to a shape of the ultrasound probe handle 302 of the ultrasound probe 300. Furthermore, in some other embodiments, an outer coating such as an outer electrically insulating cover may be disposed on an outer/exterior surface of the thermal energy storage chamber 308. Moreover, the thermal energy storage chamber 308 may form an ergonomic exterior shape of the ultrasound probe handle 302 of the ultrasound probe 300.

Accordingly, the design of the ultrasound probe 300 having the thermal energy storage chamber 308 provides enhanced thermal management in the ultrasound probe 300. As will be appreciated, the currently available techniques rely on the thermal conductivity of the material such as copper and titanium to transport the heat. However, the exemplary 3D vapor chamber 208 uses evaporation and condensation of the working fluid to transport the heat in the 3D vapor chamber 208. Consequently, use of the 3D vapor chamber 208 provides up to a 20× improvement over that provided via use of copper for heat transportation.

Furthermore, in accordance with further aspects of the present specification, in addition to facilitating enhanced thermal management in the ultrasound probe 300, the thermal energy storage chamber 308 may also be configured to provide mechanical support to the internal components of the ultrasound probe 300. This aspect will be described in greater detail with reference to FIGS. 6-9.

Figure 4:
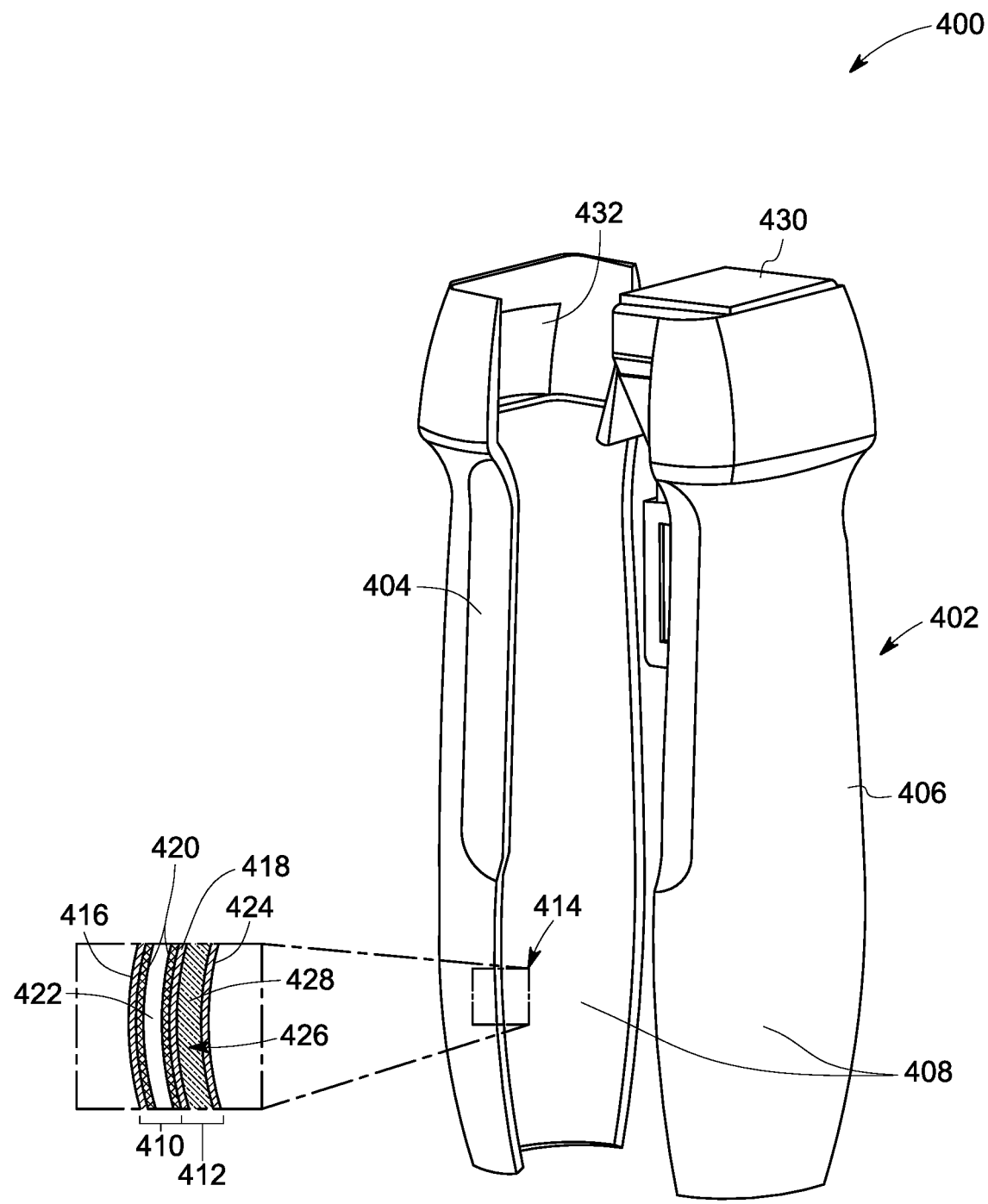

FIG. 4 is a diagrammatical illustration 400 of yet another embodiment of an ultrasound probe for use in the system 100 of FIG. 1 is depicted. FIG. 4 is described in conjunction with the components of FIGS. 1-3. In accordance with aspects of the present specification, in the embodiment 400 of FIG. 4, a phase change chamber of the ultrasound probe 400 is a nested configuration of the 3D vapor chamber 208 of FIG. 2 and the thermal energy storage chamber 308 of FIG. 3.

The ultrasound probe 400 includes an ultrasound probe handle 402. In one embodiment, the ultrasound probe handle 402 may include two or more segments that are operatively coupled to one another. In FIG. 4, the ultrasound probe handle 402 is depicted as having a first segment 404 and a second segment 406, where each segment 404, 406 is representative of one half of the ultrasound probe handle 402.

Moreover, the ultrasound probe 400 includes a thermal management assembly in the form of a phase change chamber 408 that is configured to provide enhanced thermal management for the ultrasound probe 400. The reference number 408 shown in FIG. 4 refers to the interior of the chamber. The phase change chamber 408 is monolithic with respect to a portion of the ultrasound probe handle 402 and is configured to thermally interface with one or more heat generating components in the ultrasound probe 400 to dissipate the heat generated by the components of the ultrasound probe 400. In one embodiment, the phase change chamber 408 is directly/thermally coupled to one or more components of the ultrasound probe 400 to facilitate dissipation of heat from the heat generating components of the ultrasound probe. Also, in certain embodiments, the phase change chamber 408 may include two or more phase change chambers.

In a presently contemplated configuration, the phase change chamber 408 has a nested configuration. More particularly, the phase change chamber 408 includes a 3D vapor chamber 410 such as the 3D vapor chamber 208 of FIG. 2 and a thermal energy storage chamber 412 such as the thermal energy storage chamber 308 of FIG. 3. Reference numeral 414 is used to represent an expanded view of a cross-section of one embodiment of the phase change chamber 408.

The phase change chamber 408 has hermetic chamber walls that extend around and define an enclosed chamber. In certain embodiments, the 3D vapor chamber 410 includes an external wall 416. Further, the phase change chamber 408 includes a common wall 418 that is shared by the 3D vapor chamber 410 and the thermal energy storage chamber 412. In one example, the external wall 416 and the common wall 418 form a cavity. Additionally, the 3D vapor chamber 410 includes a working fluid that is disposed within the cavity. Further, the 3D vapor chamber 410 includes a porous wick structure 420 configured to facilitate transport of the working fluid in the 3D vapor chamber 410. In particular, the porous wick structure 420 is disposed such that the porous wick structure 420 lines one or more interior surfaces of the external wall 416 of the 3D vapor chamber 410 and/or the common wall 418. Also, the porous wick structure 420 includes pores that are configured to hold the working fluid in a liquid phase in the 3D vapor chamber 410 until heat received from a heat generating component of the ultrasound probe 400 vaporizes the working fluid into a vapor phase in the enclosed 3D vapor chamber 410. Moreover, the porous wick structure 420 aids in returning the working fluid from the condenser end to the evaporator end of the 3D vapor chamber 410. In addition, the 3D vapor chamber 410 includes a vapor transport column or vapor space 422. The vapor transport column 422 is configured to aid in the transport of the working fluid in a vapor phase within the 3D vapor chamber 410.

In accordance with further aspects of the present specification, the phase change chamber 408 also includes the thermal energy storage chamber 412. Furthermore, the thermal energy storage chamber 412 has a hermetic chamber wall such as an internal wall 424. Also, a cavity 426 is formed between the common wall 418 and the internal wall 424. A phase change material 428 such as wax is housed in this cavity 426 and the phase change material 428 is configured to change phase in response to heat received from a component of the ultrasound probe 400. In particular, the phase change material 428 is configured to transition between a solid phase and a liquid phase.

It may also be noted that in some embodiments, the cavity 426 may also include fins (not shown in FIG. 4) extending from the common wall 418 and/or the internal wall 424 into the phase change material 428 to aid in heat transport to the phase change material 428. As noted hereinabove, the fins in the cavity 426 are internal fins. In this example, the fins may be in the form of studs or may extend in an annular fashion around the radius of the ultrasound probe 400. It may be noted that the annular fins may have openings or ports to facilitate filling and/or transport of the phase change material 428. Also, the fins may have a structure that is similar to the structure of the 3D vapor chamber 410 and/or the thermal energy storage chamber 412. Also, as previously noted, the phase change material 428 may also include thermally conductive fillers such as particles, spheres, and/or ribbons of graphite, copper, aluminum, and the like to improve heat transfer.

Moreover, in certain embodiments, multiple such fins may be dispersed along the length of the 3D vapor chamber 410. It may be noted the fins used in the 3D vapor chamber 410 are external fins. The fins or studs serve to increase the surface area of the 3D vapor change chamber 410, which in turn improves heat transfer. In certain embodiments, the fins and/or studs may be formed using the same material as the common wall 418, the external wall 416, and/or the internal wall 424 of the phase change chamber 408.

Furthermore, the phase change material 428 such as wax is used in the thermal energy storage chamber 412 to aid in the absorption of heat from the heat generating components of the ultrasound probe 400. The phase change material 428 is in a solid phase and housed in the cavity 426. Once the thermal energy storage chamber 412 is placed in contact with a heat source such as a heat generating component in the ultrasound probe 400, the heat from the heat source is absorbed by the phase change material 428 in the thermal energy storage chamber 412. It may be noted that in certain embodiments, the heat source may also be the heat from the 3D vapor chamber 410. The absorbed heat results in the phase change material 428 being transformed from a solid phase to a liquid phase. As previously noted, transitions between other phases and/or chemical reactions may also occur during the transportation of the heat. In some embodiments, the absorbed heat may be stored in the thermal energy storage chamber 412. However, in other embodiments, the latent heat may be transferred to an outer surface of the phase change chamber 408 and the heat is dissipated into the surrounding environment.

In accordance with farther aspects of the present specification, in some embodiments, the 3D vapor chamber 410 may be placed in direct contact with the heat dissipating component(s) in the ultrasound probe 400 (see FIG. 5) since the 3D vapor chamber 410 effectively has a very high thermal conductivity. Accordingly, the 3D vapor chamber 410 is configured to absorb the heat generated by the heat dissipating component(s) in the ultrasound probe 400. Further, in this example, the 3D vapor chamber 410 is configured to carry the absorbed heat to another part of the ultrasound probe 400 having the nested configuration of the 3D vapor chamber 410 and the thermal energy storage chamber 412, and the heat is stored in the thermal energy storage chamber 412.

As previously noted, one or more components of the ultrasound probe 400 generate heat during operation of the ultrasound probe 400. Reference numeral 430 is used to depict a heat generating component of the ultrasound probe 400 such as a transducer assembly. It is desirable to efficiently dissipate the heat generated by the transducer assembly to ensure safe and continuous operation of the ultrasound probe 400 to image the patient 102.

In accordance with aspects of the present specification, the 3D vapor chamber 410 and the thermal energy storage chamber 412 are configured to facilitate enhanced thermal management of the ultrasound probe 400. In particular, the 3D vapor chamber 410 and/or the thermal energy storage chamber 412 are configured to provide enhanced heat transfer from the heat generating components of the ultrasound probe 400 by directly thermally contacting one or more surfaces of the heat generating components of the ultrasound probe 400. In the example of FIG. 4, the transducer assembly 430 is thermally coupled to the 3D vapor chamber 410 and/or the thermal energy storage chamber 412 of the ultrasound probe 400. In one example, the transducer assembly 430 is directly thermally coupled to a portion 432 of an interior surface of the phase change chamber 408. In some embodiments, the phase change chamber 408 may be directly thermally coupled to the heat generating components via use of a thermal interface material such as thermal pads, grease, adhesive, and the like.

It may be noted that to facilitate rapid and efficient removal/dissipation of heat or thermal energy from internal components of the ultrasound probe 400, the phase change chamber 408 is formed using a material with a high thermal conductivity. By way of example, the phase change chamber 408 may be formed using materials such as, but not limited to, titanium, aluminum, copper, and the like.

Further, for ease of illustration and description, the phase change chamber 408 is depicted as including two phase change chamber portions. These portions may be sealed to form the phase change chamber 408. Accordingly, in one embodiment, the phase change chamber 408 is a continuous structure.

The ultrasound probe 400 including the ultrasound probe handle 402, the 3D vapor chamber 410 and thermal energy storage chamber 208 may be formed using additive manufacturing, such as by being formed using three-dimensional (3D) printing, rapid prototyping (RP), direct digital manufacturing (DDM), selective laser melting (SLM), electron beam melting (EBM), direct metal laser melting (DMLM), and the like. Some other exemplary methods of additive fabricating usable with the present specification may include processes, such as, but not limited to, direct writing, electron beam deposition, laser deposition, stereo-lithography, and the like. Alternatively, the ultrasound probe 400 may be formed in any another manner.

Additively manufacturing the phase change chamber 408 as described hereinabove results in a phase change chamber 408 that is a single, monolithic structure and configured to interface with one or more heat sources in the ultrasound probe 400 to facilitate the enhanced dissipation of heat generated by the internal components of the ultrasound probe 400. In particular, the phase change chamber 408 is configured to facilitate transfer of thermal energy from the heat generating components of the ultrasound probe 400 such as the transducer assembly 430 and internal electronics of the ultrasound probe 400 for dissipation, storage, or both. By way of example, the 3D vapor chamber 410 is used to absorb the heat generated by the ultrasound components and transfer the absorbed heat to an outer surface of the phase change chamber 408 for cooling by the ambient environment. Additionally, the thermal energy storage chamber 412 is used to absorb the heat generated by the ultrasound components and stored the absorbed heat in the phase change material 428.

Accordingly, the design of the ultrasound probe 400 having the 3D vapor chamber 410 and the thermal energy storage chamber 412 provides enhanced thermal management in the ultrasound probe 400. As previously noted, the currently available techniques rely on the thermal conductivity of the material such as copper and titanium to transport the heat. Also, typically, phase change materials have a poor thermal conductivity and hence need thick conducting walls or fillers within the phase change material to transport heat into the phase change material. Using the exemplary 3D vapor chamber 410 high heat transport capabilities in conjunction with the thermal energy storage chamber 412 aids in enhanced heat spreading along the phase change material 428, thereby facilitating uniform melting of the phase change material 428. Consequently, this design of the ultrasound probe 400 having the 3D vapor chamber 410 and the thermal energy storage chamber 412 results in higher heat absorption and hence longer duration of temperature control of the heat generating component.

Figure 5:
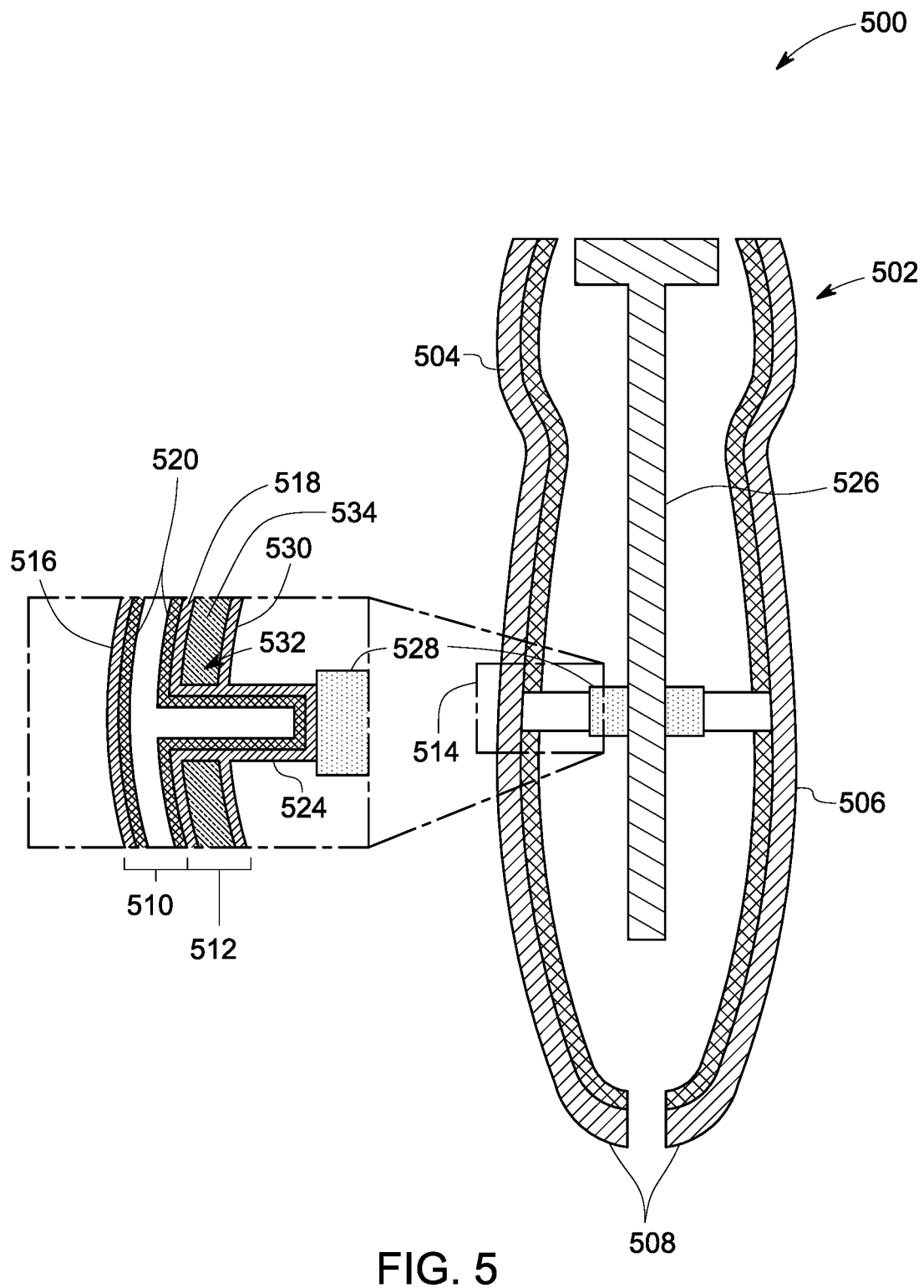

Referring now to FIG. 5, a diagrammatical illustration 500 of yet another embodiment of an ultrasound probe for use in the system 100 of FIG. 1 is depicted. FIG. 5 is described in conjunction with the components of FIGS. 1-4. In a presently contemplated configuration of FIG. 5, a phase change chamber of the ultrasound probe 500 is a nested configuration of the 3D vapor chamber 410 and the thermal energy storage chamber 412 of FIG. 4. Additionally, the 3D vapor chamber in the nested configuration includes a projection that is configured to be in thermal contact with a heat generating component of the ultrasound probe 500.

The ultrasound probe 500 includes an ultrasound probe handle 502. Also, the ultrasound probe handle 502 may include two or more segments such as a first segment 504 and a second segment 506 that are operatively coupled to one another.

In accordance with aspects of the present specification, the ultrasound probe 500 includes a thermal management assembly in the form of a phase change chamber 508 that is configured to provide enhanced thermal management for the ultrasound probe 500. The phase change chamber 508 is monolithic with respect to a portion of the ultrasound probe handle 502 and is configured to thermally interface with one or more heat generating components in the ultrasound probe 500 to dissipate the heat generated by the components of the ultrasound probe 500. As depicted in FIG. 5, the phase change chamber 508 has a nested configuration such as the nested configuration 400 of FIG. 4. More particularly, the phase change chamber 508 includes a 3D vapor chamber 510 such as the 3D vapor chamber 410 and a thermal energy storage chamber 512 such as the thermal energy storage chamber 412 of FIG. 4. An expanded view of a cross-section of one embodiment of the phase change chamber 508 is generally referenced by reference numeral 514.

Moreover, as previously noted with reference to FIG. 4, the 3D vapor chamber 510 has hermetic chamber walls that extend around and define an enclosed chamber. The 3D vapor chamber 510 includes an external wall 516. Also, the phase change chamber 508 includes a common wall 518 that is shared by the 3D vapor chamber 510 and the thermal energy storage chamber 512. Additionally, the 3D vapor chamber 510 includes a working fluid that is disposed within a cavity between the external wall 516 and the common wall 518. The working fluid is configured to change phase in response to heat received from a component of the ultrasound probe 500. Moreover, the 3D vapor chamber 510 includes a porous wick structure 520 configured to facilitate transport of the working fluid in the 3D vapor chamber 510. The porous wick structure 520 includes pores that are configured to hold the working fluid in a liquid phase in the 3D vapor chamber 510. Also, the porous wick structure 520 aids in returning the working fluid from the condenser end to the evaporator end of the 3D vapor chamber 410. Further, the 3D vapor change chamber 510 includes a vapor transport column or vapor space configured to aid in the transport of the working fluid in a vapor phase within the 3D vapor chamber 510.

In a presently contemplated configuration, one or more portions of the 3D vapor chamber 510 may extend inward from at least one of the hermetic chamber walls and at least partially towards an inner section of the ultrasound probe handle 502. This extension may be generally referred to as a projection 524. It may be noted that tier ease of illustration the configuration of the 3D vapor chamber 510 of FIG. 5 is depicted as including one projection 524. However, the 3D vapor chamber 510 may include more than one projection 524. In this embodiment, the projection 524 of the 3D vapor chamber 510 is disposed in direct thermal contact with one or more components 526 of the ultrasound probe 500 and configured to facilitate dissipation of heat generated by the components 526 of the ultrasound probe 500. In certain embodiments, the ultrasound probe 500 may also include a heat dissipating component 528. The heat dissipating component 528 is configured to thermally couple the 3D phase change chamber 510 to one or more heat generating components of the ultrasound probe 500. Accordingly, in this example, the heat dissipating component 528 is positioned in direct thermal contact with one or more heat generating components 526 of the ultrasound probe 500 and the projection 524 is thermally coupled to the heat dissipating component 528. Hence, the heat generated by the components 526 of the ultrasound probe 500 is transferred to the projection 524 in the 3D vapor chamber 510 via the heat dissipating component 528.

Additionally, the phase change chamber 508 also includes the thermal energy storage chamber 512. The thermal energy storage chamber 512 has a hermetic chamber wall such as an internal wall 530. Also, a phase change material 534 such as wax is housed in a cavity 532 that is formed between the common wall 518 and the internal wall 530. Moreover, this phase change material 534 is configured to change phase in response to heat received from a component 526 of the ultrasound probe 500. The phase change material 534 that is configured to transition between a solid phase and a liquid phase.

Further, for ease of illustration and description, the phase change chamber 508 is depicted as including two phase change chamber portions. These portions may be sealed to form the phase change chamber 508. Accordingly, in one embodiment, the phase change chamber 508 is a continuous structure.

The ultrasound probe 500 including the ultrasound probe handle 502, the 3D vapor chamber 510 and thermal energy storage chamber 512 may be formed using additive manufacturing, such as by being formed using three-dimensional (3D) printing, rapid prototyping (RP), direct digital manufacturing (DDM), selective laser melting (SLM), electron beam melting (EBM), direct metal laser melting (DMLM), and the like. Some other exemplary methods of additive fabricating usable with the present specification may include processes, such as, but not limited to, direct writing, electron beam deposition, laser deposition, stereo-lithography, and the like.

As will be appreciated, it is desirable to have an ultrasound probe that is an ergonomically sound structure and a light weight structure capable of dissipating heat generated in the ultrasound probe by transferring and/or storing the generated heat to an outer surface of the ultrasound probe, and subsequently to the ambient environment. FIGS. 6-9 represent further embodiments of an ultrasound probe having a thermal management assembly in the form of an exemplary phase change chamber that is configured to provide enhanced thermal management for the ultrasound probe by facilitating enhanced dissipation and/or storage of heat generated by internal components of the ultrasound probe. It may be noted that phase change chambers depicted in FIGS. 6-9 may be created using additive manufacturing, such as by being formed using three-dimensional (3D) printing, rapid prototyping (RP), direct digital manufacturing (DDM), selective laser melting (SLM), electron beam melting (EBM), direct metal laser melting (DMLM), or the like. Alternatively, the phase change chambers can be formed in another manner.

Figure 6:
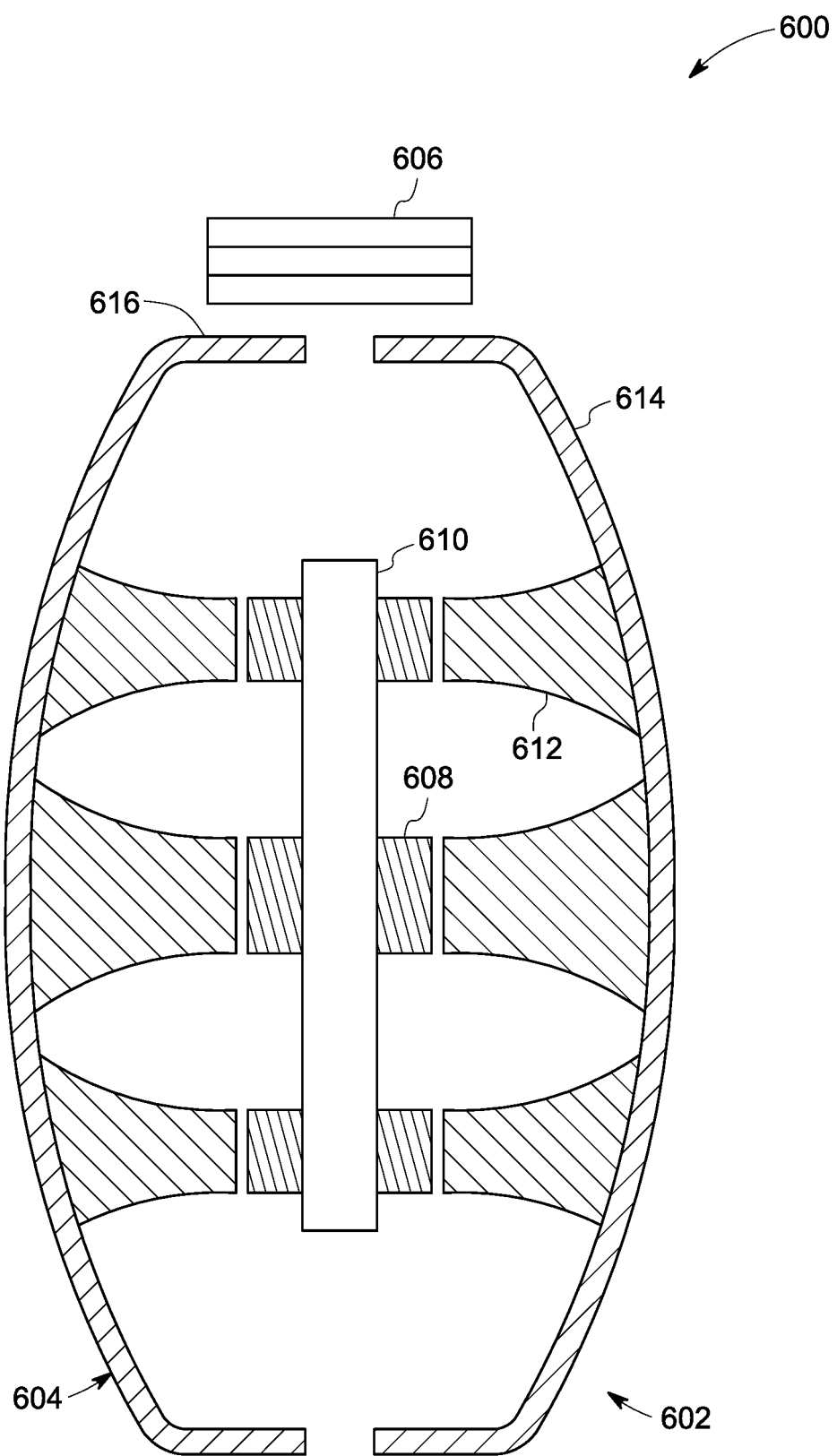
FIGS. 6-9 are cross-sectional views of different embodiments of an ultrasound probe having various configurations of a thermal management assembly in the form of a phase change chamber, where the ultrasound probe is configured for use in the system of FIG. 1, in accordance with aspects of the present specification.

Turning now to FIG. 6, a diagrammatical illustration 600 of a cross-section of one embodiment of an ultrasound probe for use in the system 100 of FIG. 1, in accordance with aspects of the present specification, is depicted. FIG. 6 is described in conjunction with the components of FIGS. 1-5.

In the example of FIG. 6, a cross-sectional view of a wireless ultrasound probe 600 is depicted. As will be appreciated, a wireless ultrasound probe 600 includes additional components such as batteries, wireless transmitters, wireless receivers, and corresponding electronics to support operation of the wireless ultrasound probe 600. Moreover, these additional components are distributed across the wireless ultrasound probe 600 serve as additional heat sources. Further, due to the additional components such as the batteries and/or wireless transmitters/receivers, the heat generated in the ultrasound probe 600 is distributed and higher in magnitude.

In the embodiment depicted in FIG. 6, the ultrasound probe 600 is depicted as including an ultrasound probe handle 602 and a thermal management assembly in the form of a phase change chamber 604 within the ultrasound probe handle walls and configured to provide enhanced thermal management for the ultrasound probe 600. In the example of FIG. 6, the phase change chamber 604 is a 3D vapor chamber configured to facilitate enhanced thermal management of the ultrasound probe 600 having the additional heat sources. As previously noted, the 3D vapor chamber 604 is monolithic with respect to at least a portion of the ultrasound probe handle 602. Additionally, the 3D vapor chamber 604 is configured to be a thermally conductive structure. In certain embodiments, the 3D vapor chamber 604 may also be configured to provide mechanical or structural support to internal components of the ultrasound probe 600.

The ultrasound probe 600 includes a transducer assembly 606, one or more processors, ASICs, batteries, sensors and the like. Components such as processors, ASICs, batteries, sensors, and the like are generally represented by reference numeral 608. Also, these components 608 may be mounted on a mother board 610. As noted hereinabove, the components 606, 608 are additional heat sources in the ultrasound probe 600 and are distributed in the volume of the ultrasound probe 600.

In the embodiment depicted in FIG. 6, the 3D vapor chamber 604 is configured to interface with the various heat sources 606, 608 within the 3D vapor chamber 604 to facilitate dissipation of heat generated by the heat sources 606, 608. To that end, the vapor chamber 604 includes one or more projections 612 configured to facilitate the enhanced transfer of heat from the heat generating internal components 606, 608 of the ultrasound probe 600. These projections 612 may be similar to the projection 524 of FIG. 5 and are depicted in greater detail in FIG. 6. In one embodiment, the projections 612 may include finger-like protrusions. Additionally, in the example depicted in FIG. 6, the projections 612 are disposed on an interior surface of the 3D vapor chamber 604 such that each projection 612 contacts at least one heat source 608. In particular, each projection 612 is thermally coupled to at least one heat source 608.

Moreover, as previously noted, the 3D vapor chamber 604 and the 3D vapor chamber projections 612 may be created using additive manufacturing, such as by being formed using three-dimensional (3D) printing, rapid prototyping (RP), direct digital manufacturing (DDM), selective laser melting (SLM), electron beam melting (EBM), direct metal laser melting (DMLM), or the like. Alternatively, the 3D vapor chamber 604 can be formed in another manner.

The design of the ultrasound probe 600 having the 3D vapor chamber 604, which in turn has the projections 612 provides a single monolithic structure configured to access multiple heat sources 608 and dissipate the heat generated by the heat sources 608. Moreover, the 3D vapor chamber 604 having the projections 612 is formed using a material having a high thermal conductivity. Consequently, the heat generated by the components 608 is efficiently transported to an outer surface of the ultrasound probe handle 602 via the projections 612 in the 3D vapor chamber 604 for dissipation into the surrounding environment.

It may be noted that the exemplary design of the 3D vapor chamber 604 aids in replacing a spine, heat spreaders, heat pipes, thermal pads, plastic PCB holders that are used in conventional ultrasound probes. Additionally, the 3D vapor chamber 604 may be used as a handle of an ultrasound probe. Moreover, the design of FIG. 6 provides the ultrasound probe 600 having the ultrasound probe handle 602 that has a lower weight, less complexity, higher thermal performance, and faster installation time compared to the conventional ultrasound probes. It may be noted that a cross-section of one embodiment of a shell 614 of the 3D vapor chamber 604 may have a structure that is substantially similar to the cross-section 214 of the 3D vapor chamber 208 of FIG. 2.

Additionally, in certain embodiments, the ultrasound probe 600 and the 3D vapor chamber 604 in particular may include a thermal mounting platform 616. In this example, the 3D vapor chamber 604 extends along the length of the ultrasound probe handle walls to the area of the thermal mounting platform 616. Further, the thermal mounting platform 616 is directly coupled to the transducer assembly 606 and configured to transfer heat generated by the transducer assembly 606 to the 3D vapor chamber 604 for dissipation to the surrounding environment. As will be appreciated, the transducer assembly 606 typically includes a stack of components such as a transducer array of one or more transducer elements, processing electronics in the form of application specific integrated circuits (ASICs), a thermal-acoustic backing, and the like (not shown in FIG. 6). The thermal-acoustic backing of the transducer assembly 606 may be mounted on and directly coupled to the thermal mounting platform 616.

The heat generated by the transducer assembly 606 is transferred from the transducer assembly 606 via the thermal-acoustic backing to the thermal mounting platform 616. The thermal mounting platform 616 in turn transfers this heat to the enclosure or shell 614 of the 3D vapor chamber 604. The enclosure 614 provides an expansive surface area for the dissipation of the heat generated by the transducer assembly 606 for cooling by the ambient environment. Also, the thermal mounting platform 616 may be formed using a strong and light weight material such as titanium. Some non-limiting examples of the material used to form the thermal mounting platform 616 include titanium, copper, aluminum, and the like. However, other materials may also be used to form the thermal mounting platform 616.

In accordance with further aspects of the present specification, in addition to facilitating enhanced thermal management in the ultrasound probe 600, the 3D vapor chamber 604 may also be configured to provide mechanical support to the internal components of the ultrasound probe 600. By way of example, the thermal mounting platform 616 in addition to facilitating dissipation of heat from the transducer assembly 606 may also be configured to provide mechanical support to the transducer assembly 606 in the ultrasound probe 600. As noted hereinabove, the thermal-acoustic backing of the transducer assembly 606 may be mounted on and directly coupled to the thermal mounting platform 616.

Figure 7:
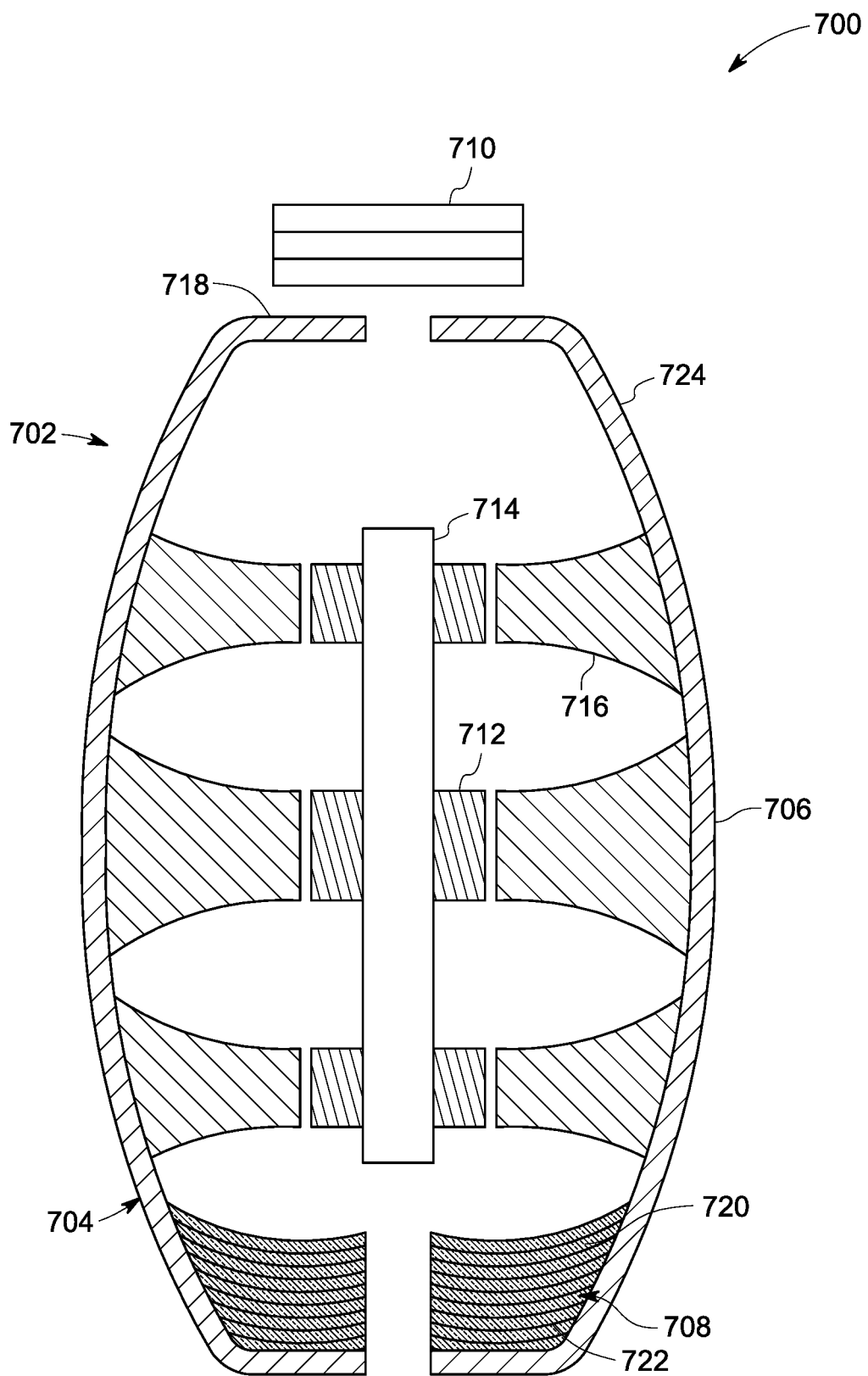
Figure 8:
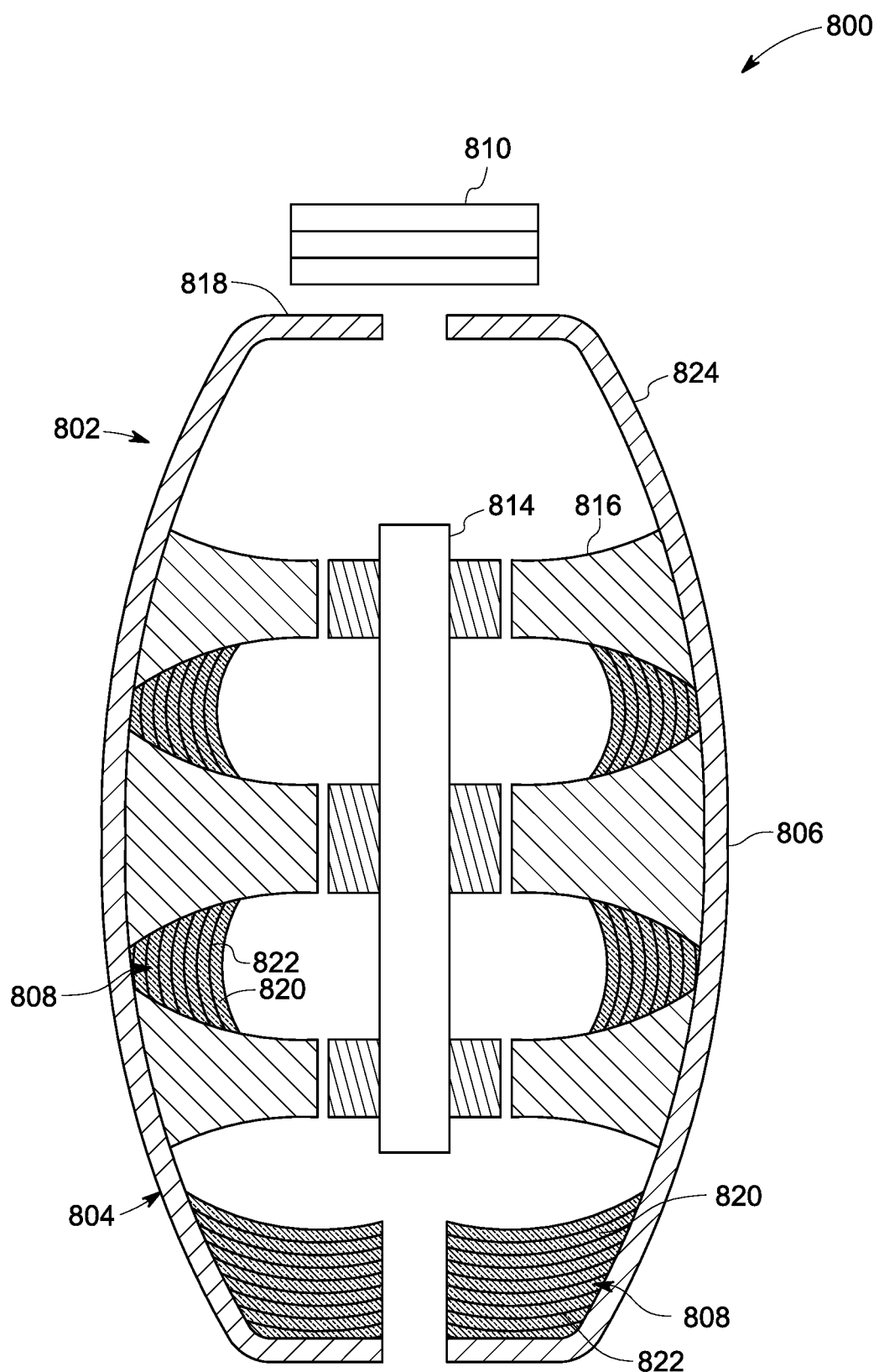
Figure 9:
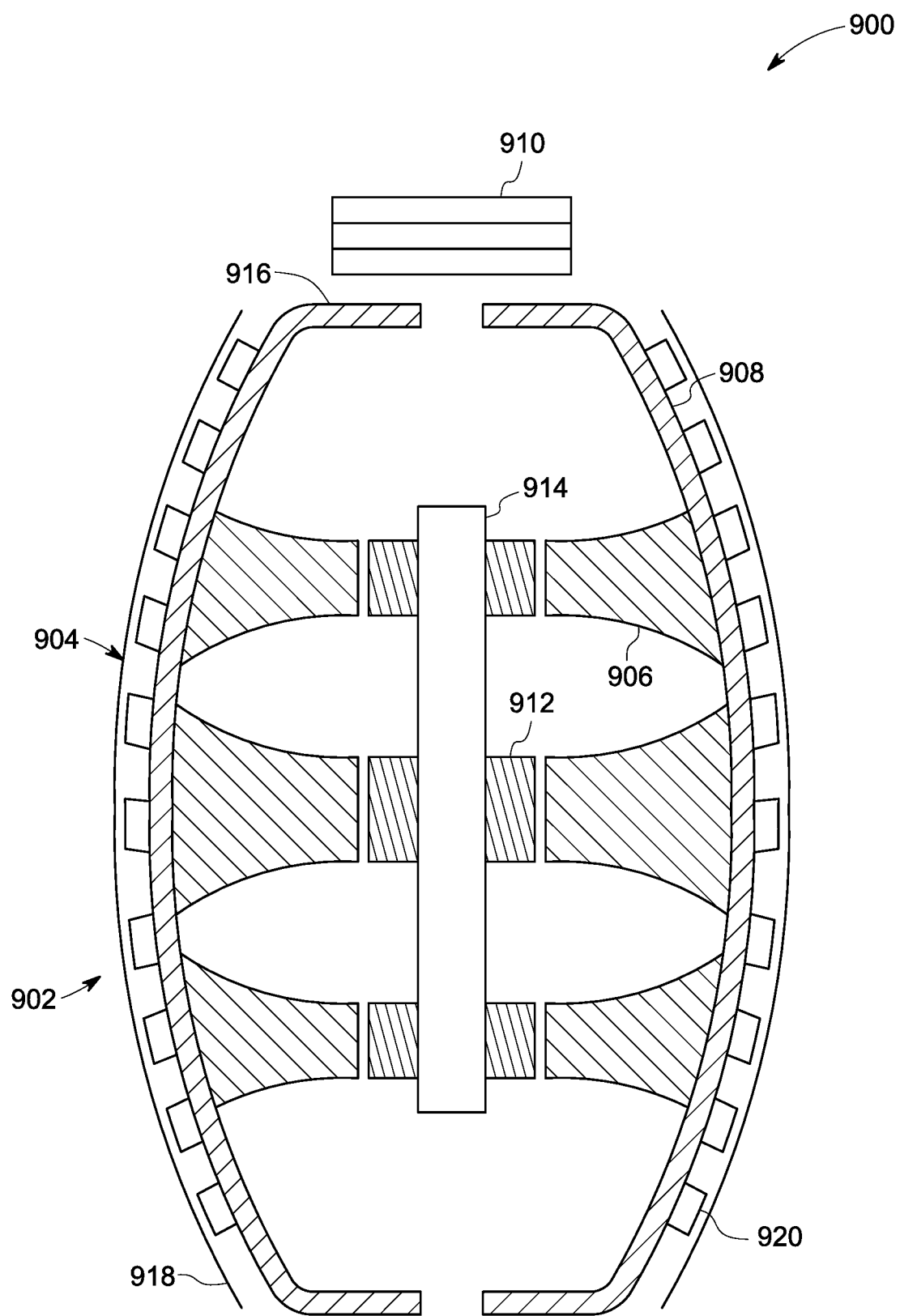

FIGS. 7-9 represent different embodiments of an ultrasound probe. In particular, embodiments of the ultrasound probe depicted in FIGS. 7-9 illustrate alternative configurations of the ultrasound probe 600 depicted in FIG. 6. In addition, a cross-section of one embodiment of the phase change chambers of the embodiments depicted in FIGS. 7-9 may have a structure that is substantially similar to the cross-sections 210, 310, 414, 514 of the phase change chambers of FIGS. 2-5.

FIG. 7 is a diagrammatical illustration 700 of a cross-section of another embodiment of an ultrasound probe, in accordance with aspects of the present specification. Also, FIG. 7 is described in conjunction with the components of FIGS. 1-6.

As previously described with reference to FIG. 6, a digital wireless probe includes additional heat sources and hence experiences a higher internal heat load. Accordingly, it is desirable that a surface area of the ultrasound probe be large enough to maintain temperatures of the ultrasound probe to a value below about 43° C.

In the embodiment depicted in FIG. 7, the ultrasound probe 700 is depicted as including ultrasound probe handle 702 and a thermal management assembly in the form of a phase change chamber 704 within walls of the ultrasound probe handle 702 and configured to provide enhanced thermal management for the ultrasound probe 700. In a presently contemplated configuration, the phase change chamber 704 includes a 3D vapor chamber 706 and a thermal energy storage chamber 708 configured to facilitate enhanced thermal management of the ultrasound probe 700 having the additional heat sources.

The ultrasound probe 700 includes a transducer assembly 710, one or more processors, ASICs, batteries, sensors, and the like. Components such as processors, ASICs, batteries, sensors and the like are generally represented by reference numeral 712. These components 712 may be mounted on a mother board 714. As noted hereinabove, the components 712 are additional heat sources in the ultrasound probe 700 and are distributed in the volume of the ultrasound probe 700.

The 3D vapor chamber 706 is configured to interface with the various heat sources 712 of the ultrasound probe 700 to facilitate dissipation of heat generated by the heat sources 712. Accordingly, the 3D vapor chamber 706 includes one or more projections 716 configured to facilitate the enhanced transfer of heat from the heat generating internal components 712 of the ultrasound probe 700. In one embodiment, the projections 716 may include finger-like protrusions. Additionally, in the example depicted in FIG. 7, the projections 716 are disposed on an interior surface of the 3D vapor chamber 706 such that each projection 716 contacts at least one heat source 712. In particular, each projection 716 is thermally coupled to at least one heat source 712.

The design of the ultrasound probe 700 having the 3D vapor chamber 706, which in turn has the projections 716 provides a single monolithic structure configured to access multiple heat sources 712 and dissipate generated by these heat sources 712. Moreover, the 3D vapor chamber 706 having the projections 716 are formed using a material having a high thermal conductivity. Consequently, the heat generated by the components 712 is efficiently transported to an outer surface of the ultrasound probe handle 702 via the projections 716 in the 3D vapor chamber 706 for dissipation into the surrounding environment.

In the example of FIG. 7, the ultrasound probe 700 and more particularly the phase change chamber 704 additionally includes the thermal energy storage chamber 708 that is configured to house a phase change material (PCM) 720. As will be appreciated, a phase change material is a material that melts and solidifies at a determined temperature and is capable of storing and releasing large amounts of energy. By way of example, heat is absorbed by the phase change material 720 when the phase change material 720 changes from a solid phase to a liquid phase at a corresponding melting temperature. Also, the stored energy is released when the phase change material 720 cools down to a corresponding freezing point to change phase from a liquid to a solid. It may be noted that in certain embodiments, the freezing point and the melting point of the phase change material 720 may be the same or different. Moreover, the phase change material 720 may include materials such as, but not limited to, organic materials, inorganic materials, metallic alloys, eutectic alloys, paraffin wax, or combinations thereof. Furthermore, in certain embodiments, the phase change material 720 may be injected into or otherwise disposed in the thermal energy storage chamber 708. In some embodiments, the phase change material(s) 720 may also be encapsulated within one or more polymeric shells. Accordingly, in this example, the phase change material(s) 720 may be referred to as encapsulated phase change material(s). Also, in one example, the one or more polymeric shells may have a size of less than or about 5 mm.

In this embodiment of the ultrasound probe 700, a portion of heat generated by the internal components 712 of the ultrasound probe 700 may be dissipated through an outer surface of the phase change chamber 704. The remaining heat is absorbed by the phase change material 720 and stored in the thermal energy storage chamber 708 as the phase change material is transitioned from a solid phase to a liquid phase.

Furthermore, in certain embodiments, the ultrasound probe 700 and the phase change chamber 704 in particular may include a thermal mounting platform 718. In this example, the thermal mounting platform 718 is directly coupled to the transducer assembly 710 and configured to transfer heat generated by the transducer assembly 710 to the 3D vapor chamber 706 for dissipation to the surrounding environment. Moreover, the thermal mounting platform 718 may also be configured to transfer heat generated by the transducer assembly 710 to the phase change material 720 for storage in the thermal energy storage chamber 708. It may be noted that in addition to facilitating enhanced thermal management in the ultrasound probe 700, the 3D vapor chamber 706 and the thermal mounting platform 718 in particular may also be configured to provide mechanical support to the internal components of the ultrasound probe 700.

Additionally, the 3D vapor chamber 706 may also include one or more fins (not shown in FIG. 7). As previously noted, the fins in the 3D vapor chamber 706 may be external fins. In this embodiment, the fins aid in dissipating the heat generated in the ultrasound probe 700. In one embodiment, the fins may be integral with an enclosure or shell 724 of the 3D vapor chamber 706. By way of a non-limiting example, the fins may be integrated with the enclosure 724 of the 3D vapor chamber 706 as a plain metal or as an extension of the 3D vapor chamber 706, similar to the projection 524 of FIG. 5. More particularly, the fins 722 are in thermal communication with the 3D vapor chamber 706 to facilitate the dissipation of heat from the heat generating components 710, 712 of the ultrasound probe 700.

Furthermore, by way of a non-limiting example, the fins may have a rectangular cross-section or a circular cross-section. Also, the fins may extend annularly along the radius of the ultrasound probe handle 702. In certain embodiments, the annular fins may have openings or ports to facilitate filling and/or transport of the phase change material 722.

In addition, the fins may also be in the form of pins and/or studs of various cross-sectional shapes that extend from the enclosure or shell 724 of the 3D vapor chamber 706 into the thermal energy storage chamber 708 such that the fins are in thermal contact with the phase change material 720. The fins may also be aligned along the length of the shell 724. In other embodiments, the fins having varying shapes and/or forms may be dispersed in a random fashion along the shell 724. These fins may be similar to the projection 524 depicted in FIG. 5.

Furthermore, in certain embodiments, the thermal energy storage chamber 708 may also include one or more of the fins 722. As previously noted, the fins 722 in the thermal energy storage chamber 708 are internal fins. In this example, the fins 722 may be optimally spaced within a volume of phase change material 720 in the thermal energy storage chamber 708 and configured to aid in dissipating heat from the phase change material 720. Also, in one embodiment, the fins 722 may be spaced uniformly within the volume of the phase change material 720 in the thermal energy storage chamber 708. However, in another embodiment, the fins 722 may be disposed with variable spacing within the volume of phase change material 720 in the thermal energy storage chamber 708. These fins 722 are configured to lower the heat conduction resistance from the 3D vapor chamber 706 to the phase change material 720 in the thermal energy storage chamber 708 and also promote uniform change in the state/phase of the phase change material 720. Moreover, the fins 722 are also in thermal communication with the phase change material 720 to facilitate the efficient bidirectional transfer of heat between the heat generating components 710, 712 of the ultrasound probe 700 and the phase change material 720. In one example, the fins 722 may aid in transferring heat from the heat generating components 710, 712 of the ultrasound probe 700 to the phase change material 720 for storage in the thermal energy storage chamber 708. In another example, the fins 722 may aid in transferring the heat stored in the phase change material 720 in the thermal energy storage chamber 708 to the components 710, 712 of the ultrasound probe 700 and/or the environment surrounding the ultrasound probe 700.

Use of the phase change material 720 in the thermal energy storage chamber 708 results in a lower surface area requirement of the ultrasound probe 700, thereby allowing the ultrasound probe 700 to be smaller in size than a corresponding size of an ultrasound probe without the phase change material 720. Moreover, a choice of the phase change material 720 may be customized based on the heat generating sources in the ultrasound probe 700. By way of non-limiting example, a phase change material 720 that is configured to melt at 35° C. may be selected. Moreover, use of the phase change material 720 advantageously provides a uniformity in temperature as the phase change processes take place over a constant temperature. Accordingly, all the components of the ultrasound probe 700 that are in contact with the phase change material 720 may be maintained at a constant temperature for a determined period of time. Hence, the ultrasound probe 700 may be maintained at near isothermal device temperatures until all the phase change material 720 has melted by transitioning from the solid phase to the liquid phase. Accordingly, in the embodiment of FIG. 7, heat generated by the transducer assembly 710 and/or the components 712 of the ultrasound probe 700 may be transferred to the 3D vapor chamber 706 for dissipation and/or to the thermal energy storage chamber 708 for storage in the phase change material 720.

Moreover, as previously noted, the phase change chamber 704 having the 3D vapor chamber 706 and the thermal energy storage chamber 708 may be created using additive manufacturing, such as by being formed using three-dimensional (3D) printing, rapid prototyping (RP), direct digital manufacturing (DDM), selective laser melting (SLM), electron beam melting (EBM), direct metal laser melting (DMLM), or the like.

Turning now to FIG. 8, a diagrammatical illustration 800 of a cross-section of yet another embodiment of an ultrasound probe, in accordance with aspects of the present specification, is depicted. FIG. 8 is described in conjunction with the components of FIGS. 1-7.

In FIG. 7, the phase change material 720 was housed n one thermal energy storage chamber 708 disposed at one end of the ultrasound probe 700. However, in accordance with further aspects of the present specification, the phase change material may also be distributed within an internal volume/surface of an ultrasound probe in one or more smaller volumes. Accordingly, in the embodiment of FIG. 8, the ultrasound probe 800 includes two or more thermal energy storage chambers disposed at different locations along the inner surface of an enclosure of a phase change chamber.

In the embodiment depicted in FIG. 8, the ultrasound probe 800 is depicted as including an ultrasound probe handle 802 and a thermal management assembly in the form of a phase change chamber 804 within the ultrasound probe handle walls and configured to provide enhanced thermal management for the ultrasound probe 800. In a presently contemplated configuration, the phase change chamber 804 includes a 3D vapor chamber 806 and two or more thermal energy storage chambers 808 configured to facilitate enhanced thermal management of the ultrasound probe 800 having the additional heat sources.

As depicted in FIG. 8, the ultrasound probe 800 includes a transducer assembly 810, one or more processors, ASICs, batteries, sensors and the like. Reference numeral 812 is used to represent components such as processors, ASICs, batteries, sensors, and the like. The components 812 are additional heat sources in the ultrasound probe 800 and are distributed in the volume of the ultrasound probe 800. Also, these components 812 may be mounted on a mother board 814.

The 3D vapor chamber 806 is configured to interface with the various heat sources 812 of the ultrasound probe 800 to facilitate dissipation of heat generated by the heat sources 812. In one embodiment, the 3D vapor chamber 806 includes one or more projections 816 such as finger-like protrusions configured to facilitate the enhanced transfer of heat from the heat generating internal components 812 of the ultrasound probe 800. Additionally, each projection 816 is configured to be thermally coupled to at least one heat source 812.

Moreover, in certain embodiments, the ultrasound probe 800 and the 3D vapor chamber 806 in particular may include a thermal mounting platform 818 that is directly coupled to the transducer assembly 810 and configured to transfer heat generated by the transducer assembly 810 to the 3D vapor chamber 806 for dissipation to the surrounding environment.

Furthermore, in the example of FIG. 8, the ultrasound probe 800 and more particularly the phase change chamber 804 additionally includes a thermal energy storage chamber 808 that is configured to house a phase change material (PCM) 820. Heat is absorbed by the phase change material 820 when the phase change material 820 changes from a solid phase to a liquid phase. Also, the stored energy is released when the phase change material 820 changes from a liquid phase to a solid phase. Moreover, the phase change material 820 may include materials such as, but not limited to, organic materials, inorganic materials, metallic alloys, eutectic alloys, paraffin wax, or combinations thereof. Furthermore, in certain embodiments, the phase change material 820 may be injected into or otherwise disposed in the thermal energy storage unit 808.

As previously noted, the heat generating components 812 are distributed within the volume of the ultrasound probe 800. Accordingly, in the example of FIG. 8, the ultrasound probe 800 additionally includes two or more thermal energy storage chambers 808 to facilitate enhanced heat dissipation from the heat generating components 812 in the ultrasound probe 800. In accordance with aspects of the present specification, the thermal energy storage chambers 808 may be distributed within the volume of the ultrasound probe handle 802.

Each of the thermal storage chambers 808 is configured to house a corresponding phase change material 820. Furthermore, each phase change material 820 may have a different phase transition temperature and may be of different types. Use of this configuration allows the added flexibility of having phase changing materials (PCMs) 820 with different melting points in each of the thermal energy storage chambers 808. By way of example, a phase change material 820 having a desired melting temperature may be selected based on a desired maximum temperature of the heat generating component 812. Consequently, the heat generating components 812 may be capped at different desirable peak temperatures by using phase change materials 820 of varying melting temperatures.

In the embodiment 800 of FIG. 8, a portion of heat generated by the internal components 812 of the ultrasound probe 800 may be dissipated through an outer surface of the 3D vapor chamber 806. The remaining heat may be absorbed by the phase change materials 820 corresponding to the different thermal energy storage chambers 808 and stored in the respective thermal energy storage chambers 808 as the phase change materials 820 are transitioned from a solid phase to a liquid phase at respective phase transition temperatures.

Moreover, in some embodiments, the phase change chamber 804 may also include one or more fins (not shown in FIG. 8) configured to aid in dissipating heat generated in the ultrasound probe 800. In one embodiment, these fins may be integral with the enclosure 824 of the 3D vapor chamber 806. Also, these fins may be external fins.

Also, in certain embodiments, each thermal energy storage chamber 808 may also include a corresponding set of fins 822. These fins 822 may be internal fins. Also, as previously noted, each set of fins 822 may be uniformly spaced or disposed with variable spacing within a volume of the corresponding phase change material 820 in the thermal energy storage chamber 808 and configured to aid in dissipating heat from the phase change materials 820. In particular, the phase change materials 820 are in thermal communication with the corresponding set of fins 822 to facilitate dissipation of heat stored within the phase change materials 820.

As will be appreciated, phase change materials are typically poor heat conductors and hence disadvantageously need internal heat spreading structures such as thermally conductive fins and foams. Advantageously, the thermal energy storage chambers 808 having the respective phase change materials 820 and the 3D vapor chamber 806 provide an ultrasound probe 800 having an enhanced heat dissipating ability. Moreover, the fins 822 provide the enhanced heat dissipating capability, thereby allowing effective storage of the heat in the phase change materials 820. Furthermore, the phase change materials 820 typically pose a containment risk as the phase change materials 820 expand while melting. However, integrating the thermal energy storage chambers 808 having the phase change materials 820 with the monolithic structure of the phase change chamber 804 alleviates any risk of leakage of the phase change materials 820, thereby obviating the need for additional components such as O-rings, fasteners, and thicker shells.

Use of the phase change material 820 in the thermal energy storage chamber 808 results in a lower surface area requirement of the ultrasound probe 800, thereby allowing the ultrasound probe 800 to be smaller in size than a corresponding size of an ultrasound probe without the phase change material 820. Moreover, a choice of the phase change material 820 may be customized based on the heat generating sources in the ultrasound probe 800. By way of non-limiting example, a phase change material 820 that is configured to melt at a desirable temperature may be selected. Also, in the embodiment of FIG. 8, heat generated by the transducer assembly 810 and/or the components 812 of the ultrasound probe 800 may be transferred to the 3D vapor chamber 806 for dissipation and/or to the thermal energy storage chambers 808 for storage.

Moreover, as previously noted, the phase change chamber 804 having the 3D vapor chamber 806 and the thermal energy storage chamber 808 may be created using additive manufacturing, such as by being formed using three-dimensional (3D) printing, rapid prototyping (RP), direct digital manufacturing (DDM), selective laser melting (SLM), electron beam melting (EBM), direct metal laser melting (DMLM), or the like.

FIG. 9 is a diagrammatical illustration 900 of a cross-section of yet another embodiment of an ultrasound probe for use in the system 100 of FIG. 1, in accordance with aspects of the present specification. Also, FIG. 9 is described in conjunction with the components of FIGS. 1-8.

According to further aspects of the present specification, the ultrasound probe 900 having an ultrasound probe handle 902 and a thermal management assembly in the form of a phase change chamber 904 that is configured to provide enhanced thermal management for the ultrasound probe 900 is depicted in FIG. 9. In the example of FIG. 9, the phase change chamber 904 is a 3D vapor chamber. Further, the 3D vapor chamber 904 includes projections finger-like protrusions 906 that are integral to an interior surface of an enclosure 908 of the 3D vapor chamber 904. Also, the ultrasound probe 900 includes a transducer assembly 910. In addition, the ultrasound probe 900 includes components 912 such as processors, ASICs, batteries, sensors and the like that may be mounted on a mother board 914. Moreover, the 3D vapor chamber 904 may include a thermal mounting platform 916 configured to facilitate dissipation of heat generated by the transducer assembly 910.

In the embodiment depicted in FIG. 9, the ultrasound probe 900 includes an outer protective shell 918 that is disposed such that the outer protective shell 918 encompasses the enclosure 908 the 3D vapor chamber 904. Additionally, the ultrasound probe 900 may also include one or more extended surfaces such as fins and/or studs 920 that are disposed at least on an outer surface of the enclosure 908 of the 3D vapor chamber 904. The fins 920 are external fins. Also, these fins and/or studs 920 aid in enhancing a contact surface area of the enclosure 908 of the 3D vapor chamber 904 with the outer protective shell 918. It may be noted that the studs and/or fins 920 may be integrated with the enclosure 908 of the 3D vapor chamber 904.

Additionally, in some embodiments, the outer protective shell 918 may be a thin plastic shell. However, in another embodiment, the outer protective shell 918 may be fabricated by dip coating the 3D vapor chamber 904 in a plastic coating. It may be noted that the outer protective shell 918 is formed such that the outer protective shell 918 conforms to a shape of the 3D vapor chamber 904 and the studs and/or fins 920 disposed thereon. Moreover, the outer protective shell 918 is configured to shield the ultrasound probe 900 from electric contact. Also, the outer protective shell 918 is configured to act as a sealing element, thereby providing hygiene benefits to the ultrasound probe 900. In addition, the material of the protective shell/coating 918 may be chosen to have anti-scratch, anti-bacterial, and/or anti-fungal properties.

Figure 10:
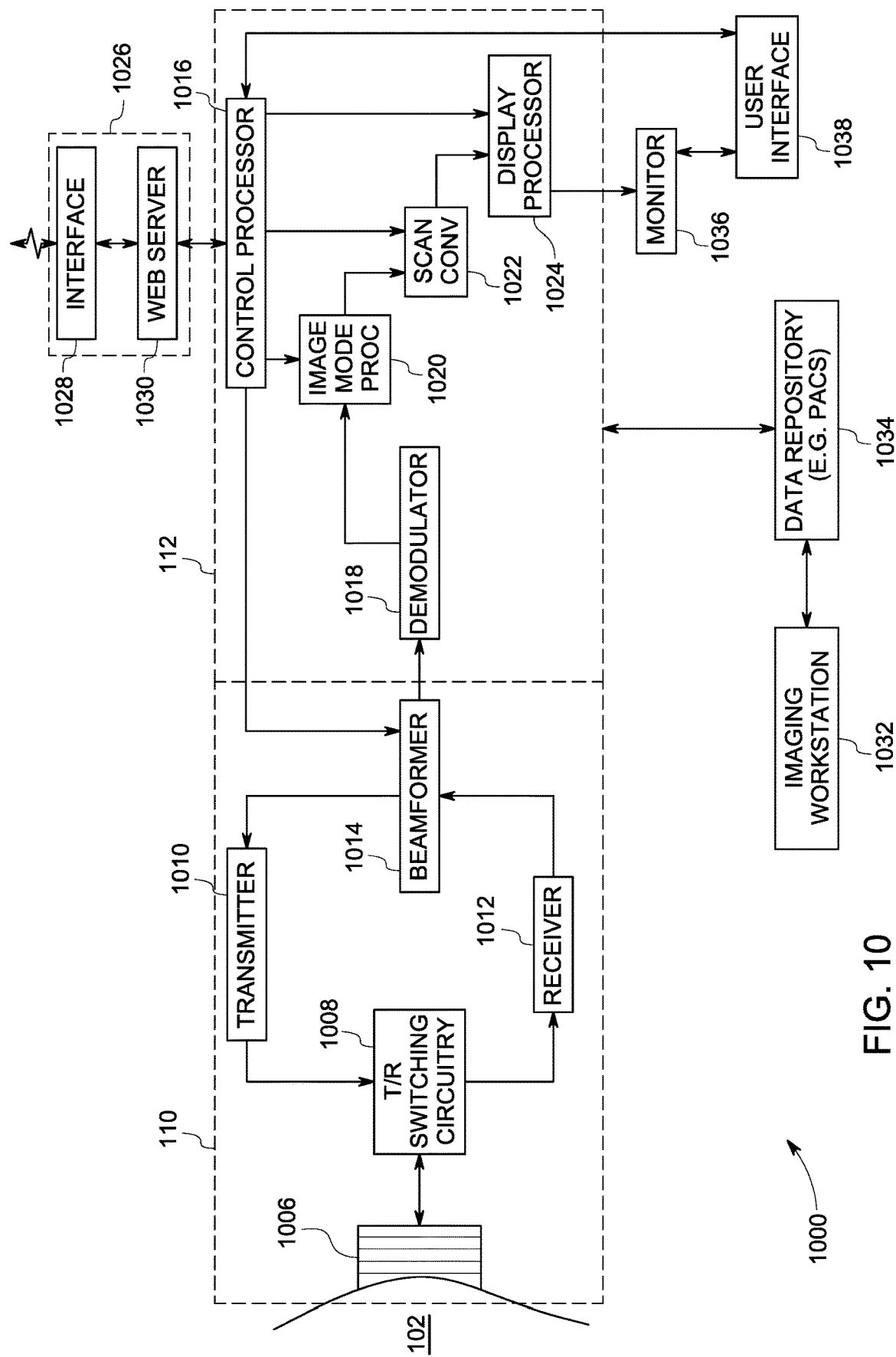
FIG. 10 is a diagrammatical illustration of an ultrasound imaging system for use in the system of FIG. 1.

As previously noted with reference to FIG. 1, the medical imaging system 108 may include an ultrasound imaging system. FIG. 10 is a block diagram 1000 of an embodiment of an ultrasound imaging system depicted in FIG. 1. The ultrasound system 1100 includes an acquisition subsystem, such as the acquisition subsystem 110 of FIG. 1 and a processing subsystem, such as the processing subsystem 112 of FIG. 1. The acquisition subsystem 110 may include a transducer assembly 1006. In addition, the acquisition subsystem 110 includes transmit/receive switching circuitry 1008, a transmitter 1010, a receiver 1012, and a beamformer 1014. It may be noted that in certain embodiments, the transducer assembly 1006 is disposed in the probe 104 (see FIG. 1). Also, in certain embodiments, the transducer assembly 1006 may include a plurality of transducer elements (not shown) arranged in a spaced relationship to form a transducer array, such as a one-dimensional or two-dimensional transducer array, for example. Additionally, the transducer assembly 1006 may include an interconnect structure (not shown) configured to facilitate operatively coupling the transducer array to an external device (not shown), such as, but not limited to, a cable assembly or associated electronics. In the illustrated embodiment, the interconnect structure may be configured to couple the transducer array to the T/R switching circuitry 1008.

The processing subsystem 112 includes a control processor 1016, a demodulator 1018, an imaging mode processor 1020, a scan converter 1022, and a display processor 1024. The display processor 1024 is further coupled to a display monitor 1036, such as the display 118 (see FIG. 1), for displaying images. User interface 1038, such as the user interface area 120 (see FIG. 1), interacts with the control processor 1016 and the display monitor 1036. The control processor 1016 may also be coupled to a remote connectivity subsystem 1026 including a remote connectivity interface 1028 and a web server 1030. The processing subsystem 112 may be further coupled to a data repository 1032, such as the data repository 116 of FIG. 1, configured to receive and/or store ultrasound image data. The data repository 1032 interacts with an imaging workstation 1034.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention. Thus, those skilled in the art will appreciate that the present ultrasound imaging system 1000 is provided by way of example, and the present specifications are in no way limited by the specific system configuration.

In the acquisition subsystem 110, the transducer assembly 1006 is in contact with the patient 102. The transducer assembly 1006 is coupled to the transmit/receive (T/R) switching circuitry 1008. Also, the T/R switching circuitry 1008 is in operative association with an output of transmitter 1010 and an input of the receiver 1012. The output of the receiver 1012 is an input to the beamformer 1014. In addition, the beamformer 1014 is further coupled to the input of the transmitter 1010 and to the input of the demodulator 1018. The beamformer 1014 is also operatively coupled to the control processor 1016 as shown in FIG. 10.

In the processing subsystem 112, the output of demodulator 1018 is in operative association with an input of the imaging mode processor 1020. Additionally, the control processor 1016 interfaces with the imaging mode processor 1020, the scan converter 1022, and the display processor 1024. An output of imaging mode processor 1020 is coupled to an input of scan converter 1022. Also, an output of the scan converter 1022 is operatively coupled to an input of the display processor 1024. The output of display processor 1024 is coupled to the monitor 1036.

The ultrasound system 1000 transmits ultrasound energy into the subject such as the patient 102 and receives and processes backscattered ultrasound signals from the subject 102 to create and display an image. To generate a transmitted beam of ultrasound energy, the control processor 1016 sends command data to the beamformer 1014 to generate transmit parameters to create a beam of a desired shape originating from a certain point at the surface of the transducer assembly 1006 at a desired steering angle. The transmit parameters are sent from the beamformer 1014 to the transmitter 1010. The transmitter 1010 uses the transmit parameters to properly encode transmit signals to be sent to the transducer assembly 1006 through the T/R switching circuitry 1008. The transmit signals are set at certain levels and phases with respect to each other and are provided to individual transducer elements such as the source elements of the transducer assembly 1006. The transmit signals excite the transducer elements to emit irradiating energy or waves with the same phase and level relationships. As a result, a transmitted beam of irradiating energy is formed in the patient 102 within a scan plane along a scan line when the transducer assembly 1006 is acoustically coupled to the patient 102 by using, for example, ultrasound gel. The process is known as electronic scanning.

The transducer assembly 1006 may be a two-way transducer. When the irradiating energy is transmitted into the patient 102, the tissue being imaged may absorb at least a portion of the delivered irradiating energy. The absorbed energy may result in a thermoelastic expansion of the tissue, which in turn results in the generation of acoustic or ultrasound waves. The acoustic or ultrasound waves may be detected by the detector elements in the transducer assembly 1006. The transducer assembly 1006 and more particularly, the detector elements in the transducer assembly 1006 may be configured to receive the acoustic waves at different times, depending on the distance into the tissue they return from and the angle with respect to the surface of the transducer assembly 1006 at which they return. The detector elements may be configured to convert the ultrasound energy from the acoustic waves into electrical signals.

The electrical signals are then routed through the T/R switching circuitry 1008 to the receiver 1012. The receiver 1012 amplifies and digitizes the received signals and provides other functions such as gain compensation. The digitized received signals corresponding to the backscattered waves received by each transducer element at various times preserve the amplitude and phase information of the backscattered waves.

The digitized signals are sent to the beamformer 1014. The control processor 1016 sends command data to beamformer 1014. The beamformer 1014 uses the command data to form a receive beam originating from a point on the surface of the transducer assembly 1006 at a steering angle typically corresponding to the point and steering angle of the previous irradiating energy transmitted along a scan line. The beamformer 1014 operates on the appropriate received signals by performing time delaying and focusing, according to the instructions of the command data from the control processor 1016, to create received beam signals corresponding to sample volumes along a scan line in the scan plane within the patient 102. The phase, amplitude, and timing information of the received signals from the various transducer elements may be used to create the received beam signals.

The received beam signals may be communicated to the processing subsystem 112. The demodulator 1018 demodulates the received beam signals to create pairs of I and Q demodulated data values corresponding to sample volumes within the scan plane. Demodulation is accomplished by comparing the phase and amplitude of the received beam signals to a reference frequency. The I and Q demodulated data values preserve the phase and amplitude information of the received signals.

The demodulated data is transferred to the imaging mode processor 1020. The imaging mode processor 1020 uses parameter estimation techniques to generate imaging parameter values from the demodulated data in scan sequence format. The imaging parameters may include parameters corresponding to various possible imaging modes such as B-mode, color velocity mode, spectral Doppler mode, and tissue velocity imaging mode, for example. The imaging parameter values are passed to the scan converter 1022. The scan converter 1022 processes the parameter data by performing a translation from scan sequence format to display format. The translation includes performing interpolation operations on the parameter data to create display pixel data in the display format.

The scan converted pixel data is sent to the display processor 1024 to perform any final spatial or temporal filtering of the scan converted pixel data, to apply grayscale or color to the scan converted pixel data, and to convert the digital pixel data to analog data for display on the monitor 1036. The user interface 1038 is coupled to the control processor 1016 to allow a user to interface with the ultrasound system 1000 based on the data displayed on the monitor 1036.

Figure 11:
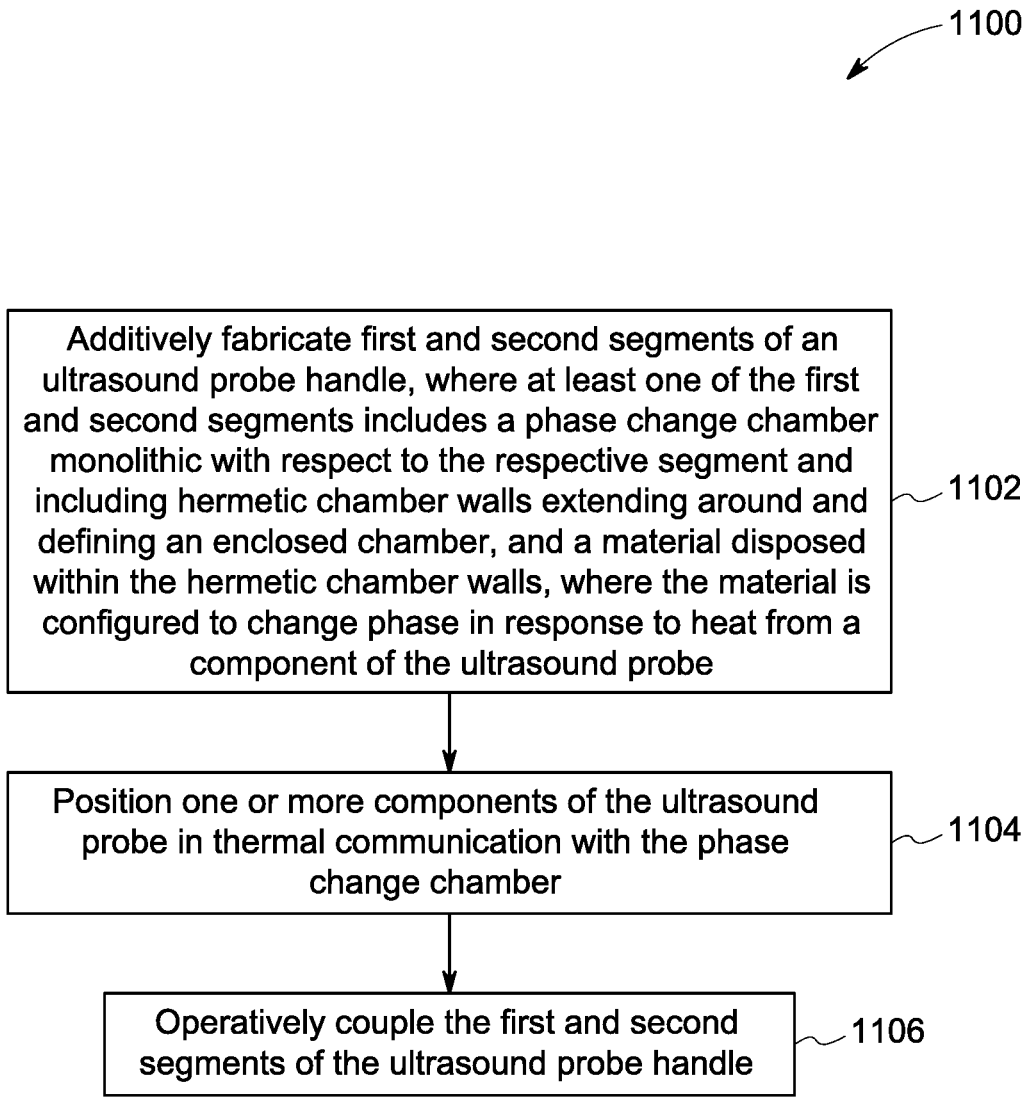
FIG. 11 is a flow chart depicting a method for manufacturing an ultrasound probe having an exemplary phase change chamber, in accordance with aspects of the present specification.

FIG. 11 is an example flow chart 1100 of a method of additive fabrication of an ultrasound probe having an ultrasound probe handle and a thermal management assembly in the form of a phase change chamber that is configured to provide enhanced thermal management for the ultrasound probe, in accordance with aspects of the present specification.

At step 1102, the method commences by additively fabricating first and second segments of an ultrasound probe handle. It may be noted that at least one segment of the first and second segments of the ultrasound probe handle includes a phase change chamber. The phase change chamber is monolithic with respect to the corresponding segment. Moreover, the phase change chamber includes hermetic chamber walls that extend around and define an enclosed chamber. In certain embodiments, the phase change chamber may be a 3D vapor chamber, a thermal energy storage chamber, or a combination thereof.

Furthermore, a material is disposed within the hermetic chamber walls. The material is configured to change phase in response to heat received from a component of the ultrasound probe. Also, the material may include a working fluid and/or a phase change material. Various embodiments of the phase change chamber have been described with reference to FIGS. 2-9. If the phase change chamber is a 3D vapor change chamber, the material is a working fluid that is filled in the 3D vapor chamber. The working fluid has a liquid phase and a vapor phase and is configured to facilitate the dissipation of heat from the heat generating components of the ultrasound probe. Also, if the phase change chamber includes one or more thermal energy storage chambers, the material is a phase change material that may be filled in each of the thermal energy storage chambers. The phase change materials are configured to absorb and store at least a portion of the heat generated in the ultrasound probe and facilitate storage of the absorbed heat.

Additionally, the phase change chamber having the 3D vapor chamber and/or and the thermal energy storage chamber may be created using additive manufacturing, such as by being formed using three-dimensional (3D) printing, rapid prototyping (RP), direct digital manufacturing (DDM), selective laser melting (SLM), electron beam melting (EBM), direct metal laser melting (DMLM), or the like. In one embodiment, a single three-dimensional model of the ultrasound probe handle and/or the phase change chamber to be formed may be obtained. Further, the ultrasound probe handle may be additively fabricated based on the 3D model.

Further, as previously noted, the phase change chamber is configured to facilitate enhanced transfer of heat from the heat generating components of the ultrasound probe. Accordingly, at step 1104, one or more components of the ultrasound probe may be positioned in thermal communication with the phase change chamber. Some non-limiting examples of the components of the ultrasound probe include a transducer assembly, ASICs, processors, batteries, sensors, and the like. Also, in some embodiments, the processor, the battery, the sensor, and/or the ASIC may be mounted on a support platform such as a mother board.

In particular, the phase change chamber is thermally coupled to one or more heat generating components of the ultrasound probe. In some embodiments, the phase change chamber may be directly thermally coupled to the heat generating components via use of a thermal interface material. Some non-limiting examples of the thermal interface material include thermal pads, grease, adhesive, and the like. For example, an adhesive material may be employed to form a thin adhesive joint between the phase change chamber and the heat generating components of the ultrasound probe. The adhesive material includes non-conductive epoxy, conductive epoxy, filled epoxy, and the like. Moreover, at step 1106, the first and second segments of the ultrasound probe handle may be operatively coupled to form the ultrasound probe handle of the ultrasound probe.

Also, in certain other embodiments, the method further includes additively fabricating one or more fins on the inner surface and/or the outer surface of the phase change chamber. These fins aid in further enhancing the heat dissipation capability of the vapor chamber. Moreover, the method may also include providing an outer protective shell such that the outer protective shell encompasses the enclosure of the vapor chamber.

Furthermore, the foregoing examples, demonstrations, and process steps such as those that may be performed by the system may be implemented by suitable code on a processor-based system, such as a general-purpose or special-purpose computer. It should also be noted that different implementations of the present specification may perform some or all of the steps described herein in different orders or substantially concurrently, that is, in parallel. Additionally, the functions may be implemented in a variety of programming languages, including but not limited to Ruby, Hypertext Preprocessor (PHP), Perl, Delphi, Python, C, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by the processor-based system to execute the stored code. Note that the tangible media may include paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

It may be noted that the foregoing examples, demonstrations, and process steps that may be performed by certain components of the present systems, for example by the processing subsystem 112 may be implemented by suitable code on a processor-based system. The processor-based system, for example, may include a general-purpose or a special-purpose computer. It may also be noted that different implementations of the present specification may perform some or all of the steps described herein in different orders or substantially concurrently.

Systems and methods of the present application present an exemplary design of a 3D thermal management system in the form of a 3D phase change chamber that is configured to provide a thermal management assembly/structure for an ultrasound probe. As will be appreciated, an important factor that restricts the use of ultrasound has been the fact that performing ultrasound scanning requires extended operation of an ultrasound probe at high power to render higher image resolution, while maintaining the surface and key component temperatures under their respective limits. The exemplary design of the phase change chamber provides enhanced heat transport from internal components of the ultrasound probe to an exterior/outer surface of the phase change chamber for cooling by the ambient environment and/or to phase change material volumes for thermal energy absorption/storage. Additionally, the phase change chamber forms an ergonomic exterior shape of a handle of the ultrasound probe and replaces multiple components such as heat spreaders, heat pipes, spine, PCB holder, and the associated interfaces that are used in traditional ultrasound probes. The phase change chamber provides a simplified structure of an ultrasound probe that results in reduced installation time and can accommodate additional heat loads. Additionally, the phase change chamber may also be configured to provide a mechanical support structure for the ultrasound probe.

Although specific features of embodiments of the present specification may be shown in and/or described with respect to some drawings and not in others, this is for convenience only. It is to be understood that the described features, structures, and/or characteristics, illustrated in the figures and described herein, may be combined and/or used interchangeably in any suitable manner in the various embodiments, for example, to construct additional assemblies and methods for use in diagnostic imaging.

While only certain features of the present specification have been illustrated and described herein, many modifications and changes will occur to those skilled in the art. It is, therefore, to be understood that the appended claims are intended to cover all such modifications and changes as fall within the true spirit of the invention.

The invention claimed is:

1. An ultrasound probe, comprising:
   a transducer assembly including one or more individual transducer elements;
   an inner wall and an outer wall defining an enclosed phase change chamber between the inner wall and the outer wall, wherein the inner wall is in thermal communication with the transducer assembly, wherein the outer wall functions as an ultrasound probe handle, wherein the inner wall and the outer wall defining the phase change chamber are formed from a metal with thermal conductivity, wherein the inner wall extends along an entirety of a length of the outer wall from a first side of the ultrasound probe to an opposite, second side of the ultrasound probe, and wherein the inner wall and the outer wall are hermetic walls; and
   a material disposed within the phase change chamber, wherein the material is configured to change phase in response to heat from a component of the ultrasound probe.

2. The ultrasound probe of claim 1, wherein the inner wall is coupled to the outer wall at the first side and the second side of the ultrasound probe, and wherein the phase change chamber extends along the entirety of the length of the outer wall.

3. The ultrasound probe of claim 2, wherein the ultrasound probe handle comprises a first segment and a second segment coupled together, and wherein the phase change chamber is collectively defined by the first segment and the second segment coupled together.

4. The ultrasound probe of claim 2, wherein the inner wall is in direct thermal communication with the transducer assembly and the phase change chamber is between the inner wall and the outer wall, wherein the transducer assembly is positioned at the first side of the ultrasound probe, wherein the outer wall includes a third side and a fourth side each extending along an entirety of the length of the outer wall, and wherein the inner wall is coupled to the outer wall along the third side and the fourth side.

5. The ultrasound probe of claim 1, wherein the phase change chamber comprises a vapor chamber extending along at least two orthogonal dimensions, wherein the material comprises a working fluid disposed in the vapor chamber, wherein the working fluid can be in a liquid phase or a gas phase, and wherein the working fluid is configured to transition between the liquid phase and the gas phase in response to heat.

6. The ultrasound probe of claim 5, wherein the vapor chamber further comprises a porous wick structure disposed inside and lining one or more interior surfaces of the inner and outer walls, and wherein the porous wick structure comprises pores configured to hold the liquid phase of the working fluid inside the vapor chamber.

7. The ultrasound probe of claim 1, wherein the phase change chamber is configured to store thermal energy.

8. The ultrasound probe of claim 1, further comprising a plurality of fins in thermal communication with the phase change chamber and configured to transfer heat between one or more components of the ultrasound probe and the phase change chamber, wherein the plurality of fins extend into the phase change chamber from an inner surface of the outer wall and/or an inner surface of the inner wall, and wherein the plurality of fins is distributed along a length of the phase change chamber.

9. The ultrasound probe of claim 1, wherein the phase change chamber includes a 3D vapor chamber and a thermal energy storage chamber separated by a common wall, and wherein the material disposed within the phase change chamber includes a first material disposed within the 3D vapor chamber and a second, different material disposed within the energy storage chamber.

10. The ultrasound probe of claim 1, wherein the phase change chamber is vacuum sealed.

11. The ultrasound probe of claim 1, wherein the component comprises the transducer assembly, a processor, a battery, a sensor, an application specific integrated circuit, or combinations thereof, and wherein the phase change chamber has a shape that corresponds to a shape of the outer wall.

12. The ultrasound probe of claim 11, further comprising a thermal mounting platform coupled to the phase change chamber, wherein the thermal mounting platform is directly coupled to the transducer assembly and configured to transfer heat generated by the transducer assembly to the phase change chamber.

13. The ultrasound probe of claim 1, wherein the phase change chamber comprises an additively manufactured structure such that each of the inner wall and outer wall is monolithic.

14. The ultrasound probe of claim 1, wherein the inner wall and the outer wall together form a shell, an outer surface of the shell being the outer wall, the phase change chamber being a space between the inner wall and the outer wall and entirely within the shell.

15. The ultrasound probe of claim 1, wherein the phase change chamber further includes a projection in direct thermal contact with the component, and wherein the projection comprises a portion of the phase change chamber that extends inward at least partially towards an inner section of the ultrasound probe.

16. The ultrasound probe of claim 1, further comprising a heat dissipating component, wherein the heat dissipating component is in direct contact with both the phase change chamber and the component.

17. The ultrasound probe of claim 1, wherein the metal is one of titanium, aluminum, or copper.

18. The ultrasound probe of claim 1, wherein the phase change chamber is a three-dimensional (3D) vapor chamber.

* * * * *